(12) United States Patent
Raveché

(10) Patent No.: US 6,184,372 B1
(45) Date of Patent: Feb. 6, 2001

(54) ANTISENSE INTERLEUKIN 10 AND METHODS OF USE

(75) Inventor: Elizabeth S. Raveché, Hoboken, NJ (US)

(73) Assignee: University of Medicine & Dentistry of New Jersey, Newark, NJ (US)

(*) Notice: Under 35 U.S.C. 154(b), the term of this patent shall be extended for 0 days.

(21) Appl. No.: 08/980,975

(22) Filed: Nov. 20, 1997

Related U.S. Application Data

(63) Continuation-in-part of application No. 08/608,132, filed on Feb. 28, 1996, now abandoned.

(51) Int. Cl.$^7$ .......................... C07H 21/04; C07H 21/02; A61K 48/00
(52) U.S. Cl. ...................... 536/24.5; 536/24.5; 536/24.3; 536/23.1; 435/91.1; 514/44
(58) Field of Search ............... 514/44; 435/91.1, 435/440, 375, 325; 536/24.5, 23.1, 24.3

(56) References Cited

U.S. PATENT DOCUMENTS 5,776,451 * 7/1994 Hsu et al. ..................... 424/85.2

OTHER PUBLICATIONS

Crooke, S., Basic Principles of Antisense Therapeutics, Springer–Verlag Berlin Heidelberg New York, Jul. 1998.*

Gura T., Antisense Has Growing Pains, Science, vol. 270, pp. 575–577, Oct. 1995.*

Crooke, S. et al., Antisense '97: A roundtable on the state of the industry, Nature Biotechnology, vol. 15, p.522, Jun. 1997.*

Branch, A., A good antisense molecule is hard to find, TIBS vol. 23, pp. 47–49, Feb. 1998.*

* cited by examiner

Primary Examiner—Nancy Degen
Assistant Examiner—Janet L. Epps
(74) Attorney, Agent, or Firm—Richard R. Muccino

(57) ABSTRACT

The present invention pertains to a method for treating a patient with a disease in which the levels of interleukin-10 need to be down-regulated which comprises adminstering to the patient a therapeutically effective amount of an antisense oligodeoxynucleotide specific for interleukin-10 mRNA. The present invention also pertains to an antisense oligodeoxynucleotide specific for interleukin-10 mRNA having the formula 5'-TGGGTCTTGGTTCTCAGCTTGGGGCAT (SEQ ID NO:1).

1 Claim, 23 Drawing Sheets

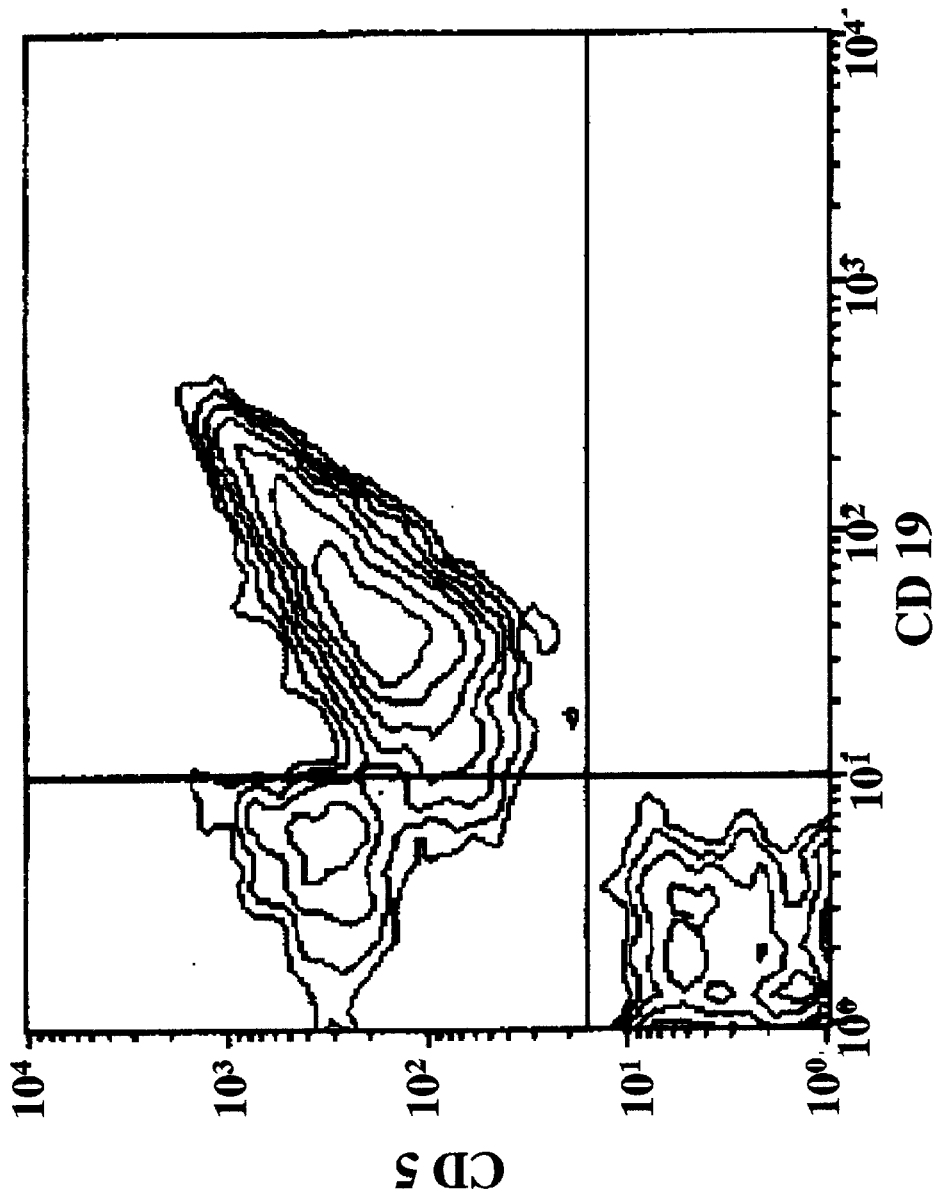

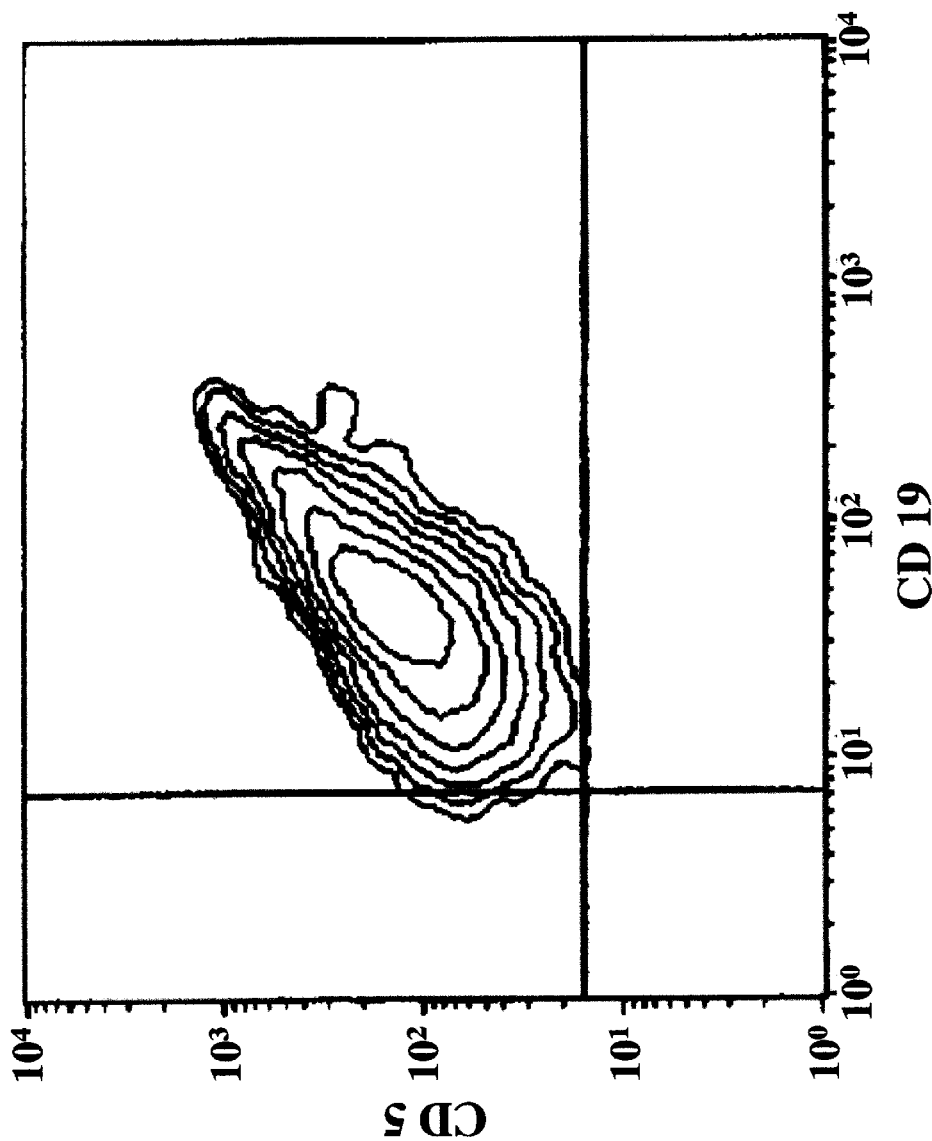

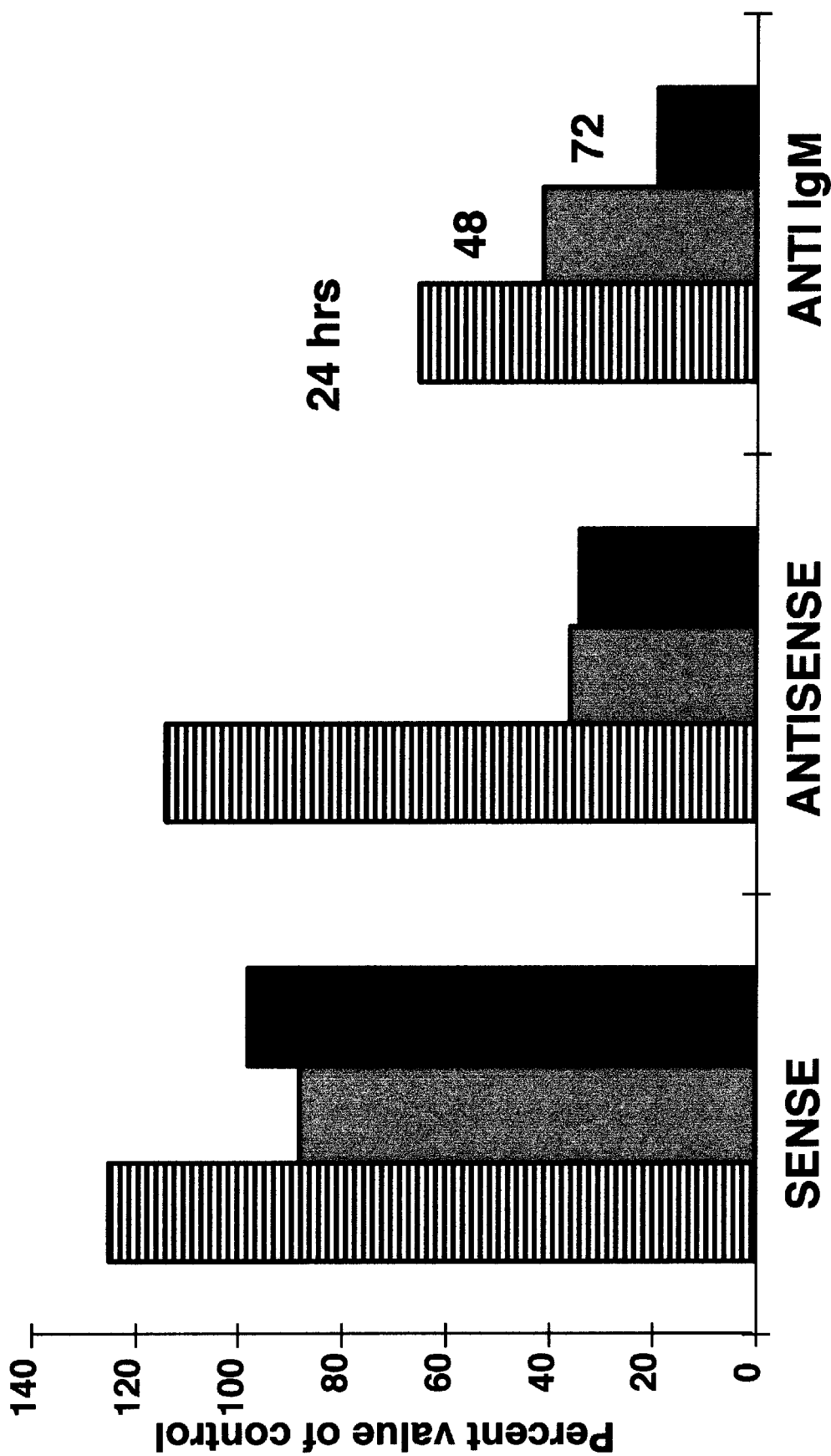

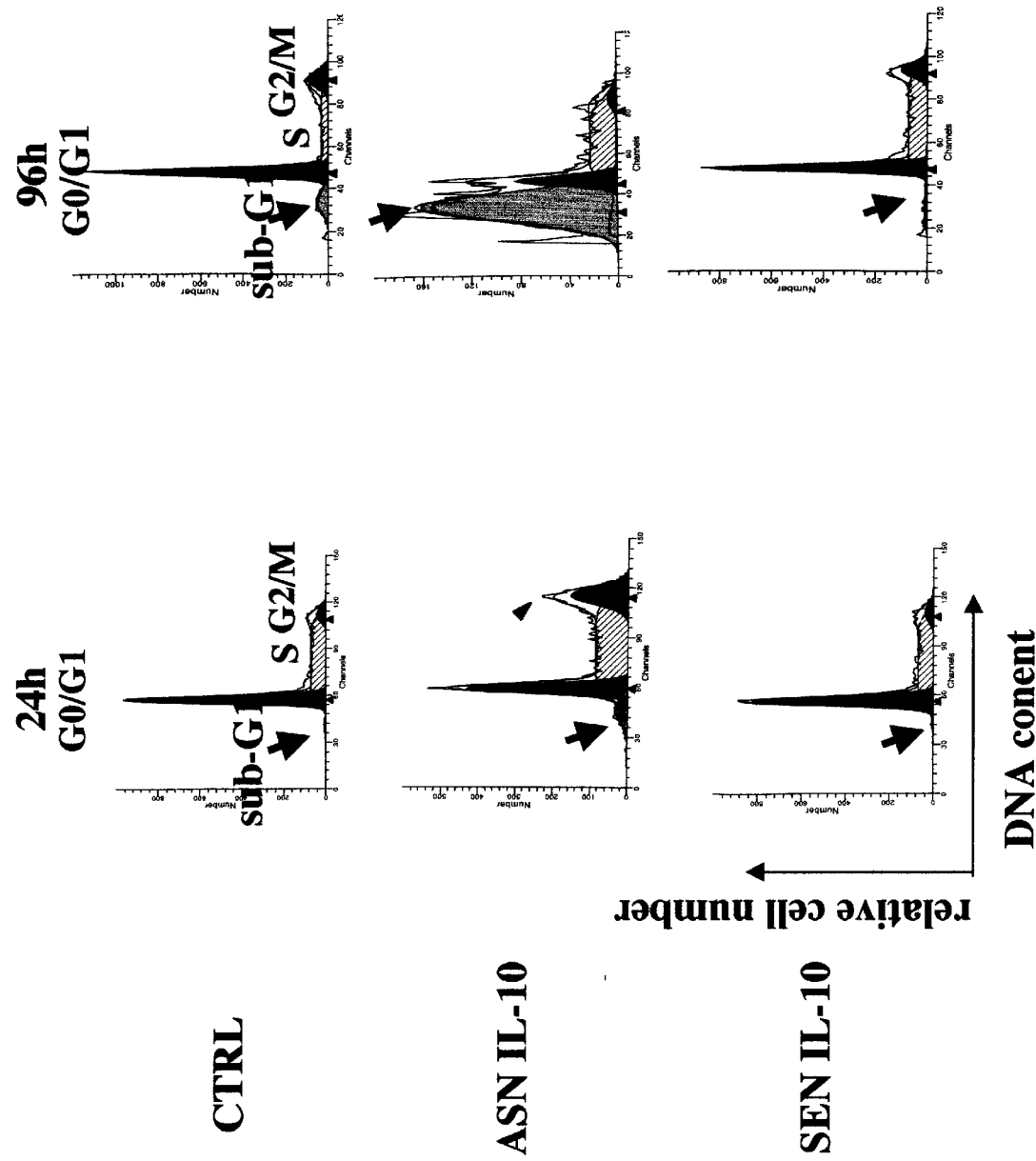

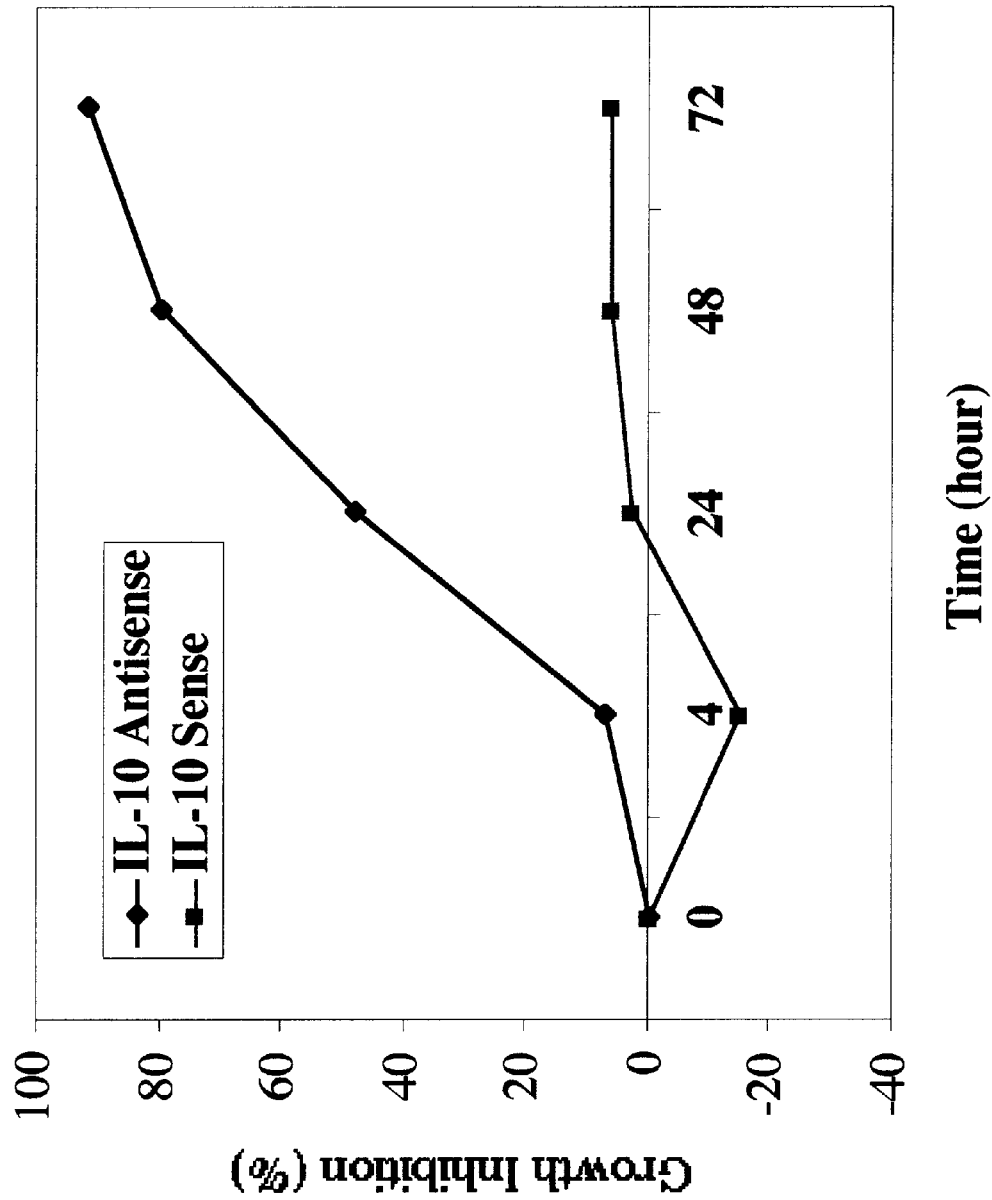

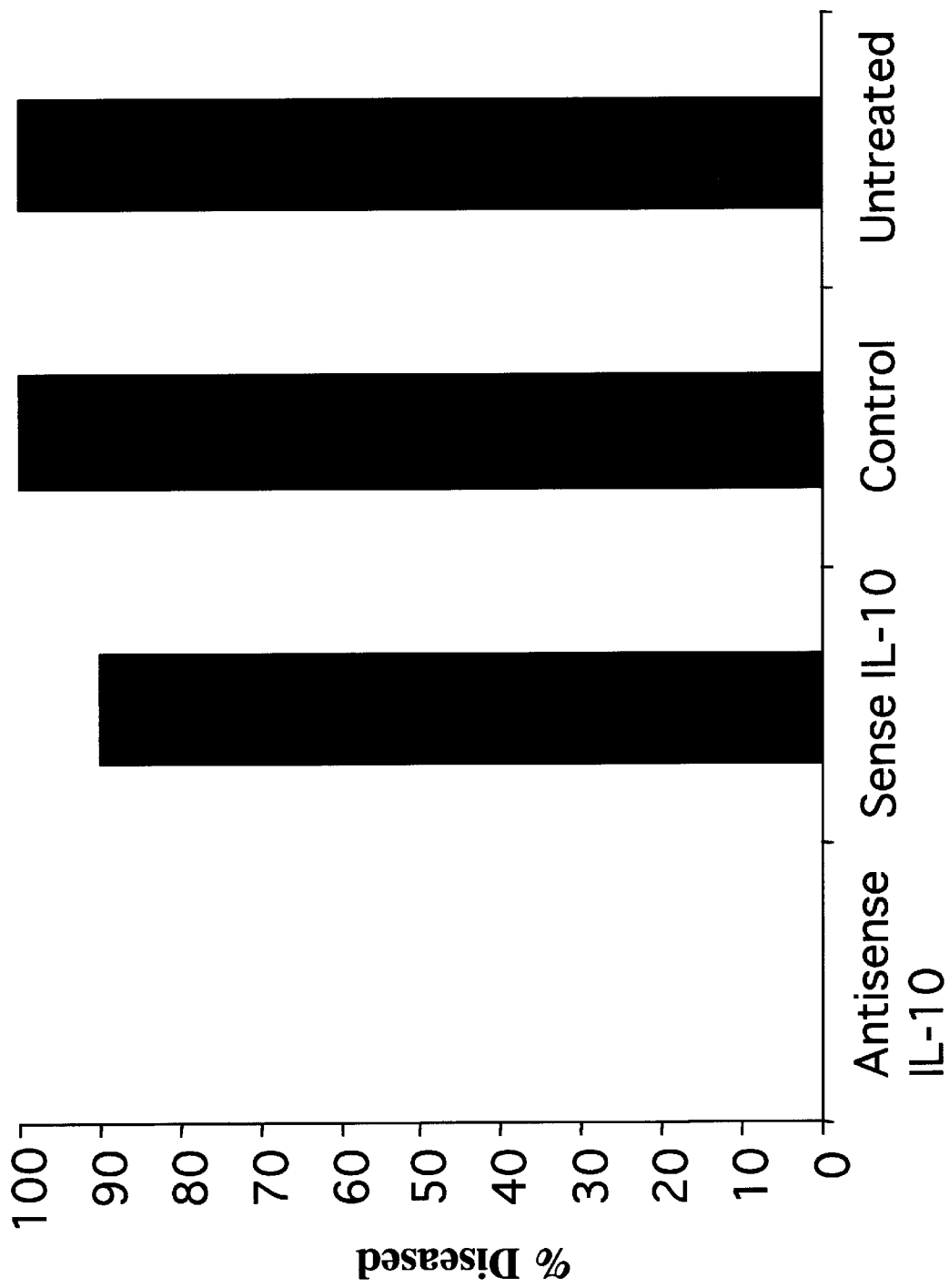

US 6,184,372 B1

ANTISENSE INTERLEUKIN 10 AND METHODS OF USE

This application is a continuation-in-part of application Ser. No. 08/608,132, filed Feb. 28, 1996, now abandoned.

STATEMENT OF RIGHTS TO INVENTIONS MADE UNDER FEDERALLY-SPONSORED RESEARCH AND DEVELOPMENT

Part of the work performed during development of this invention utilized United States Government funds. The United States Government has certain rights in this invention: NIH grant no. AI-29740 and a grant from the New Jersey Cornmission on Cancer Research.

BACKGROUND OF THE INVENTION

1. Field of the Invention

The present invention pertains to a method for treating a patient with a disease in which the levels of interleukin-10 need to be down-regulated which comprises adminstering to the patient a therapeutically effective amount of an antisense oligodeoxynucleotide specific for interleukin-10 mRNA. The present invention also pertains to an antisense oligodeoxynucleotide specific for interleukin-10 mRNA having the formula 5'-TGGGTCTTGGTTCTCAGCTTGGGGCAT (SEQ ID NO: 1).

2. Description of the Background

The disclosures referred to herein to illustrate the background of the invention and to provide additional detail with respect to its practice are incorporated herein by reference and, for convenience, are numerically referenced in the following text and respectively grouped in the appended bibliography.

Growth Inhibition of Malignant CD5+B(B-1) Cells by Antisense Interleukin-10

The increased proliferation and longevity of malignant cells is, in part, due to increased production of, or response to, growth factors. Antisense oligodeoxynucleotides which interfere with mRNA translation of growth factors are an area of intensive investigation. Of particular interest is the role of antisense directed toward the cytokine interleukin-10 (IL-10), an important regulator of B cell growth and differentiation in malignant B-1 cells.

B-1 cells are thought to belong to a sub-population of B cells. These cells are usually of a larger size, CD5+ (B-1a) or CD5− (B-1b), according to the new nomenclature (1). Due to their long life span and self-renewal capabilities, B-1 cells have an increased ability to clonally expand and become malignant. The most striking example of malignant transformation of a B-1 cell is seen in human chronic lymphocytic leukemia (CLL), where the predominant malignant cell is a B-1 cell (2). Malignant clonal expansions of B-1 cells in aged NZB mice can serve as a model for human chronic lymphocytic leukemia (3, 4). NZB mice have similarities with chronic lymphocytic leukemia patients in that there is an age-dependent onset of clonal expansion of malignant B-1 cells, the indolent course, the presence of increased numbers of lymphocytes and "smudge" cells in the circulation, and the similar pathology with malignant cells infiltrating spleen, lymph nodes and bone marrow. In both the mouse model and patients with chronic lymphocytic leukemia, occasionally the malignancy can evolve into an aggressive diffuse large cell lymphoma termed Richter's syndrome (3). Both NZB malignant B-1 cells and human chronic lymphocytic leukemia cells have been found to express IL-10 mRNA (5–7). Genetic analysis of the NZB mice have revealed a strong correlation between high levels of IL-10 and B cell lymphoproliferative disease. IL-10 antisense was found to block cell growth in murine malignant NZB B-1 cells but have only a minimal effect on non-malignant B-1 cells (51).

IL-10 is a B cell growth regulatory cytokine that can be produced by many kinds of cells including Th2 cells, macrophages, monocytes, mast cells and B cells (8–11). Among murine B cells, B-1 cells are considered the main source of B cell derived murine interleukin-10 (mIL-10) (12) while in humans, B cells induced to produce human interleukin-10 (hIL-10) are associated with the mature B and preplasmocytic stages (13). IL-10 has been found to participate in the EBV transformation of human B cells and in the development of B cell lymphomas in AIDS patients (56–58). IL-10 not only functions as a potent growth and differentiation factor for activated human B lymphocytes but it also plays a regulatory role on human monocytes (14, 15). IL-10 can function alone or together with other cytokines (15–17). In addition, exogenous IL-10 down regulates the production of IFN-gamma (15).

Gene sequencing has revealed that hIL-10 has homology to BCRF1 of Epstein-Barr virus (EBV) ard the BCRF1 expressed protein has IL-10 activity (18). Furthermore, EBV transformed B lymphocytes constitutively secrete IL-10 and there is a relationship between IL-10 production by human malignant B cell lines and EBV expression (13, 19). Therefore, B cell transformation and abnormal proliferation is related to BEV infection and the consequent elevated IL-10 expression. Addition of viral IL-10 antisense prevented EBV induced B cell transformation (20). Evidence that IL-10 plays a role in malignant B cell transformation is found in AIDS associated B cell lymphomas in which increased hIL-10 has been found (19). Recently, the use of antisense in the treatment of diseases has been extensively investigated as a potential therapy (19–21). IL-10 antisense has been shown to inhibit the cell growth of non-Hodgkin's lymphoma from AIDS patients (21). Sirtilarly, antisense IL-6 has also been shown to have growth inhibitory effects on c ells from Hairy cell leukemia and various other malignancies, such as ovarian cancer, renal cancer, and myeloma cells (22–25).

Antisense Interleukin-10 Effects on Chronic Lymphocytic Leukemia Cell Growth In the human malignancy, B-chronic lymphocytic leukemia (B-CLL), the malignant cell is a CD5+B cell. Morphological evidence as well as the phenotypic features of the circulating malignant cell in B-chronic lymphocytic leukemia suggest that the norrnal equivalent population is represented by resting CD5+B cells (43). In adult lymphoid tissues, CD5+B cells, or B-1 cells as they are referred to, are located at the edge of the germinal centers and within the mantle zone of secondary follicles. Like their normal B-1 counterparts, B-chronic lymphocytic leukemia cells coexpress CD5 and low levels of sIg, produce polyreactive antibodies and are capable of capping surface Ig. However, other features of B-chronic lymphorytic leukemia such as poor response to mitogenic stimuli, spontaneous proliferative responses to IL-2 and induction of apoptosis via Ig crosslinking are characteristic of an "activated" phenotype.

The increased proliferation and longevity of malignant cells is partly due to increased production of, or response to, growth factors. Additionally, failure to undergo programmed cell death may be due to abnormal expression of bcl-2 which plays a role in the accumulation of malignant CD5+B cells (44, 45). Consequently, antisense oligodeoxynucleotides that interfere with mRNA translation of growth factors, are candidates for therapy to regulate malignant cell growth.

SUMMARY OF THE INVENTION

The present invention pertains to a method for treating a patient with a disease in which the levels of interleukin-10 need to be down-regulated, such as diseases in which interleukin-10 is an autocrine growth factor for malignant cells or diseases wherein the inflammatory response is suppressed. The method for treating a patient with a disease wherein elevated levels of interleukin-10 has a detrimental effect, such as aquired inmmunodeficiency syndrome (AIDS), comprises adminstering to the patient a therapeutically effective amount of an antisense oligodeoxynucleotide specific for interleukin-10 mRNA.

The present invention also pertains to a method for treating a patient with chronic lymphocytic leukemia which comprises administering to the patient a therapeutically effective amount of an antisense oligodeoxynucleotide specific for interleukin-10 mRNA.

The present invention further pertains to an antisense oligodeoxynucleotide specific for interleukin-10 mRNA having the formula 5'-TGGGTCTTGGTTCTCAGCTTGGGGCAT (SEQ ID NO: 1).

BRIEF DESCRIPTION OF THE FIGURES

FIG. 9 is a graph illustrating flow cytometric analysis of cells obtained from the peripheral blood of a patient with B-chronic lymphocytic leukemia. Panel B (upper) is a contour plot of unpurified PBL. Panel B (lower) is obtained following purification of B cells as described in the Materials and Methods.

FIG. 10 is a graph illustrating representative data on growth inhibition following culturing of the PBL from an individual B-chronic lymphocytic leukemia patient.

FIG. 13 is a graph illustrating the induction of apoptosis in malignant B-1 cells in vitro.

FIG. 18 is a graph summarizing in vivo antisense IL-10 experiments including both forms of delivery, pumps and cochleates.

DETAILED DESCRIPTION OF THE INVENTION

Figure 1:
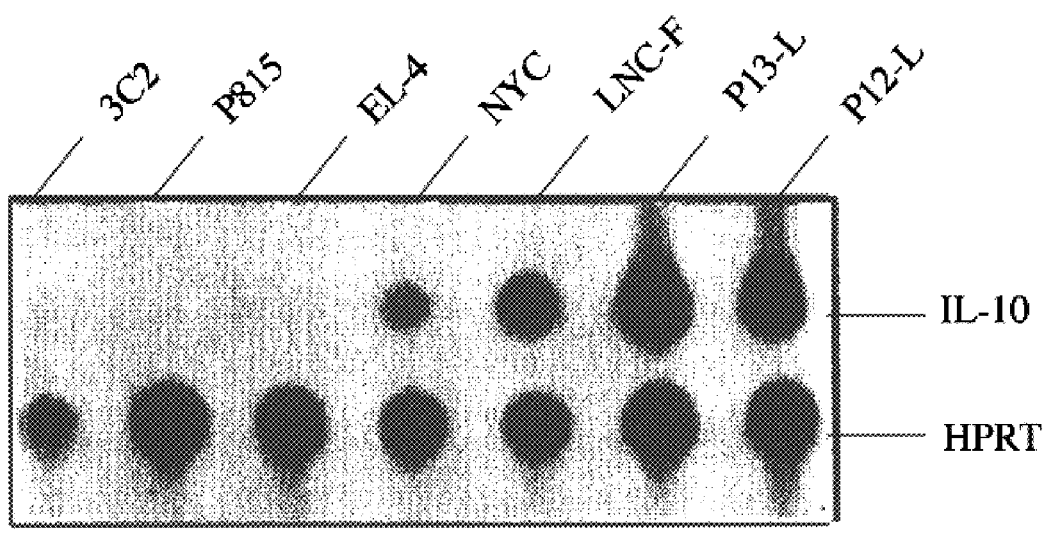
FIG. 1 is a photograph illustrating a Southern blot of mInterleukin-10 and HPRT RT-PCR products from various cell lines.

The present invention pertains to the use of antisense oligodeoxynucleotides specific for interleukin-10 mRNA in the treatment of patients with chronic lymphocytic leukemia. Interleukin-10 may be an autocrine growth factor for malignant B-1 cells and antisense therapy directed at interleukin-10 may be a potential tool in modulation of some B cell leukemias. Antisense interleukin-10 inhibits the growth of malignant B-1 cells and leads to cell death of malignant B-1 cells in some patients with chronic lymphocytic leukemia.

Malignant B-1 cells derived from NZB mice, a murine model of chronic lymphocytic leukemia. produce significantly higher levels of IL-10 mRNA than normal B-1 or B cells. IL-10 may act as an autocrine growth factor for malignant B-1 cells. By addition of antisense oligodeoxynucleotides specific for IL-10 mRNA, applicants were able to dramatically inhibit the growth of leukemic B-1 cells in a time and dose dependent manner. Control cell lines which do not depend on IL-10 for growth were not affected. Antisense therapy targeted at the 5' region of the IL-10 mRNA not only resulted in inhibition of malignant B-1 cell proliferation but also inhibited IL-10 production by malignant B-1 cells. Because endogenous IL-10 gene activation is critical for B-1 cell expansion, inactivation of the endogenous IL-10 gene by IL-10 antisense rather than extracellular regulation of the IL-10 gene product should be successful in controlling the malignant growth. From this NZB mouse model, applicants have established several in vitro cell lines that maintain the growth characteristics and cytokine profiles of the in vivo clones. Since both the in vivo and in vitro B-1 malignant cells had very high levels of IL-10 compared to non-malignant B or B-1 cells (3, 6), the use of IL-10 antisense to block cell growth was investigated.

The role of IL-10 on the in vitro growth of B cells from patients with B-chronic lymphocytic leukemrlia (CLL) was then investigated. In the present invention, peripheral blood cells from chronic lymphocytic leukemia patients were found to be varied in the ariount of IL-10 mRNA present. Several chronic lymphocytic leukemia samples underwent apoptosis in response to culturing in the presence of antisense IL-10. There was a correlation between the levels of IL-10 mRNA and the sensitivity to growth inhibition by antisense IL-10. This may indicate that antisense IL-10 inhibits cell growth in a sub-population of chronic lymphocytic leukemia in which IL-10 is an autocrine cytokine. An antisense therapy directed at the growth factors produced by malignant cells should be a way to control the growth of these cells. Therefore applicants proposed an antisense oligodeoxynucleotide (oligo) therapy to block the translation of IL-10 mRNA and inhibit the growth of malignant B-1 cells. As a result, applicants inhibited the growth of malignant B-1 cells in vitro. Therefore, IL-10 most likely plays a role as an autocrine growth factor for malignant B-1 cells and IL-10 antisense therapy could be a very promising tool in treating B cell leukemias.

NZB mice develop a B-1 cell lymphoproliferative disorder and serve as a murine model of chronic lymphocytic leukemia (CLL). The malignant B-1 cells have high expression of the cytokine IL-10, which appears to be a requisite growth factor. In the present experiments, in vitro malignant B-1 cell lines derived from the NZB mice were induced to undergo apoptosis in the presence of antisense IL-10. In vivo antisense IL-10 was delivered to mice expanding an NZB malignant B-1 clone. Two different methods of delivering antisense IL-10 were employed, all of which were effective in preventing the growth of the malignant B-1 cells. Mini-osmotic pumps which constantly deliver a steady amount of phosphorothioate-modified oligo (300 ug/day, total 8.4 mg) were effective in preventing death of the animal due to uncontrolled growth of transferred B-1 malignant cells. In these experiments at approximately 6 weeks, at which time the control animals all had died, the antisense IL-10 treated group had no evidence of disease. In addition, doses lower than 300 ug/day were not as effective in suppressing the growth of the malignant B-1 cells. An alternative form of delivery was the lipid complex called a cochleate, in which the antisense IL-10 is incorporated into the central cavity of the cochleate. Injection of antisense IL-10 in the cochleate on Days 0, 5, 8, and 14 (a total of 1.3 mg) was more efficient than the mini-osmotic pumps in protection. Possible therapeutic effects of antisense IL-10 can be considered based on the in vivo findings in the murine model of B cell lymphoproliferative disease.

Abbreviations used herein are: CLL, chronic lymphocytic leukemia; EBV, Epstein-Barr virus; oligo, oligodeoxynucleotide; MTT, (3-(4,5-dimethylthiazol-2-yl)-2,5-diphenyl tetrazoliumbromide); OD, Optical density; RT-PCR, reverse transcription-polymerase chain reaction; HPRT, hypoxanthine phosphoribosyl transferase; PBS, phosphate buffered saline; AS, antisense oligodeoxynucleotide; SS, sense oligodeoxynucleotide; CC, medium control; SO, scrambled oligodeoxynucleotide; rIL-10, recombinant murine IL-10; hIL-10, human IL-10; mIL-10, murine IL-10.

In a specific embodiment, the present invention is directed to a method for treating a patient with a disease in which the levels of interleukin-10 need to be down-regulated which comprises administering to the patient a therapeutically effective amount of an antisense oligodeoxynucleotide specific for interleukin-10 mRNA. Specifically, the disease may be a disease in which interleukin-10 is an autocrine growth factor for malignant cells or a disease in which the inflammatory response is suppressed. Preferably the disease is a disease in which interleukin-10 is an autocrine growth factor for malignant cells or is aquired inmmunodeficiency syndrome. Preferably, the malignant cells are B-1 cells and the disease is chronic lymphocytic leukemia. The antisense oligodeoxynucleotide specific for interleukin-10 mRNA may span the region adjacent to the initiation site of interleukin-10 translation, preferably region 1–500, more preferably region 310–347, and most preferably region 315–342. In a specific embodiment, the anitisense oligodeoxynucleotide is 5'-TGGGTCTTGGTTCTCAGCTTGGGGCAT (SEQ ID NO: 1).

The present invention is further illustrated by the following examples which are not intended to limyit the effective scope of the claims. All parts and percentages in the examples and throughout the specification and claims are by weight of the final composition unless otherwise specified.

EXAMPLES

Growth Inhibition of Malignant CD5 +B (B-1) Cells by Antisense Interleukin-10

Cells Lines: NZB derived malignant B-1 cells:

P12-L and P13-L are aggressive malignant B-1 cell lines derived in our laboratory and serve as in vitro leukemic cell lines (11). P12-L was derived from cells of an (NZB×DBA/2) F1 mouse lymph node expanding a hyperdiploid B-1 clone which originated from an NZB. P12-L is CD5 negative and stromal cell dependent. P13-L, which is CD5+ and non-stromal cell dependent, was derived from a (NZB×DBA/2) F1, recipient of P12-L and possesses the same immunoglobulin as P12-L. Thus, P13-L is considered a sister cell line of P12-L (6). P12-L and P13-L have been carried in vitro for over one year. To avoid the possibility that the observed effects of IL-10 antisense were due to alterations which might have occurred during in vitro long-term culture, another freshly established malignant CD5+ B-1 cell line, 275T was also tested.

Control Cell Lines:

In order to assess whether the effect of antisense is specific, various control cell lines were employed in these experiments including B cells, fibroblasts, mast cells and T cells which have been previously shown to be capable of producing IL-10 or interacting with IL-10 (10, 11, 26). a) NYC is a B cell lymphoma cell line derived from an (NZB×NZW) F1 mouse and serves as a malignant B cell control. NYC was kindly supplied by Dr. Hans-Martin Jack, Loyola University, Chicago, Ill. b) LNC-F is a stromal cell line that supports the growth of P12-L cells. P12-L cells are stromal cell dependent and readily undergo apoptosis when treated with anti-IgM. LNC-F is derived from the P12-L cell culture by repeatedly treating the P12-L cell culture with anti-IgM. LNC-F has been shown to be free of P12-L cells (6). c) P815 (from ATCC) is a mastocytoma cell line and is included as a control because IL-10 is a potential stimulatory factor for mast cells (11). d) T cell controls included: EL-4 (from ATCC) is a thymoma cell line, and 3C2 is a cytotoxic T cell line generated in our laboratory that recognizes NZB malignant B-1 cells (including P12-L cells).

P12-L, P13-L, 275T, LNC-F, EL-4 and P815 were cultured in Iscove's modified Dulbecco's medium (IMDM) from GibcoBRL, Grand Island, N.Y.; NYC and 3C2 were cultured in RPMI 1640 medium. All media supplemented with 10% heat inactivated FBS (Hyclone, Logan, Utah, USA.) and 100 U/ml penicillin/streptomycin. In the case of 3C2, the media was supplemented by the addition of 10%

Con A stimulated rat spleen cell supernatant (Con A-free) and 10 U/ml of mouse recombinant IL-2 (Genzyme, Cambridge, Mass., USA.).

Oligodeoxynucleotides:

Based on the reported sequence of murine IL-10 (27), several antisense oligos were employed. IL-10 antisense I (ASI) and sense II (SSII) are the same sequences as primers used for IL-10 PCR (28). The IL-10 antisense oligos employed were chosen because they had a lack of homology to any other murine gene sequences reported in the GENBANK DNA database. The antisense/sense oligo pairs spanned regions close to the initiation site of IL-10 translation rather than the termination site (which occurs at residue 610). IL-10 antisense I (ASI) (5'-CATTTCCGATAAGGCTTGG) (SEQ ID NO: 2) and sense I (SSI) (5'-CCAAGCCTTATCGGAAATG) (SEQ ID NO: 3) (regions 315–333); IL-10 antisense II (ASII) (5'-CGATTATTGTCTTCCCG) (SEQ ID NO: 4) and sense II (SSII) (5'-CGGGAAGACAATAACTG) (SEQ ID NO: 5) (regions 147–163); and a scrambled oligo (SO), (5'-TTTATTGCGCACGACGGAT) (SEQ ID NO: 6) which has the same base content of IL-10 ASI were used. All oligos were synthesized by Operon Technologies Inc. (Alameda, Calif., USA). Oligos were diluted in medium and added at concentrations indicated at the beginning (time 0) of culture. For the study of the effects of exogenous IL-10, recombinant murine IL-10 (rIL-10), (PharMingen, San Diego, Calif., USA.) was added at time 0 with or without oligos at concentrations indicated.

MTT Assay:

The MTT (3-(4,5-dimethylthiazol-2-yl)-2,5-diphenyl tetrazolium bromide) quantitative colorimetric assay was used to detect living, but not dead cells and the signal generated is dependent on the degree of activation of the cells and thus can be used to measure cytotoxicity, proliferation or activation (29). In order to detect the cellular growth and survival, MTT assay was performed according to published techniques with slight modifications (30). Briefly, cells ($1\times10^4$/well) were cultured with or without oligos for various times, then 20 μl of MTT (5 mg/ml in PBS, Sigma, St. Louis, Mo., USA) were added and the cells cultured in 37° C. for an additional 4 hours. In some experiments, cultures were exposed to oligos for a specified time followed by centrifugation, washing 2× and resuspension in fresh media. In these experiments, sense, antisense and media control groups were handled in a similar manner. The culture supernatants were gently flicked out and 150 μl of PBS were added and the plates were centrifuged for 5 minutes at 2000 rpm. The PBS was removed. 100 μl of 100% 2-propanol were added and vigorously pipetted to dissolve the formazan crystals. Plates were stored in dark for 30 minutes at room temperature and read at 570 nm with a reference at 650 nm on a Kinetic MicropleLte reader (Molecular Devices, Menlo Park, Calif., USA). Optical density (OD) was determined and background values subtracted.

Quantification of Cytokine Message Levels by PCR Analysis:

Total RNA was prepared using RNAzol B according to the manufacturer's specifications (TEL-Test, Friendswood, Tex., USA). Reverse transcription and PCR were performed according to the manufacturer's instructions included with the Perkin Elmer Cetus GeneAmp RNA PCR kit (Perkin Elmer Cetus Corp., Norwalk, Conn., USA). All primers and probes were synthesized by Operon Technologies Inc. (Alameda, Calif., USA). IL-10 and HPRT primers and probes employed have previously beein described (28). PCR sample quality was examined on a 2% NuSieve agarose gel (FMC Bioproducts, Rockland, Me., USA) using ethidium bromide and transferred to nitrocellulose (Schleicher and Schuell, Keene, N.H., USA) and probed with $^{32}$P-labeled internal oligo probes, which hybridized to a portion of the amplified segment between the nucleotide sequences complementary to the primers.

ELISA for Interleukin-10 andl IFN-gamma Detection

P12-L cells ($1\times10^4$ cell/ml) were incubated with either antisense or sense oligos, or medium alone for 24, 48, and 72 hours. After each time interval, supernatants were collected, concentrated (5×) and measured for IL-10 and IFN-gamma levels using a murine IL-10 ELISA kit from Endogen (Boston, Mass., USA) and a murine IFN-gamma ELISA kit from Genzyme (Cambridge, Mass., USA). The IL-10 ELISA utilized was capable of detecting a minimum of 0.14 U/ml of IL-10. The IFN-gamma ELISA utilized was capable of detecting a minimum of 125 pg/ml of IFN-gamma. Known positive and negative controls were employed. Due to the limited level of detection of the ELISA kits and the low number of the cells in culture ($1\times10^4$/ml), 5 times concentrated supernatants of the culture and medium alone for control were employed.

FIG. 1 is a photograph illustrating a Southern blot of mIL-10 and HPRT RT-PCR products from various cell lines. RNAs from various cell lines studied were extracted using R-PAzolB according to the manufactures protocol. An RT-PCR amplification was carried out with primers specific for mIL-10 and HPRT using an RT-PCR kit. PCR products were examined by Southern blot analysis using mIL-10 and HPRT specific $^{32}$P labeled internal oligo probes. Equal amounts of mIL-10 and HPRT PCR products were used and the detection of HPRT is for semiquantitative purposes.

Figure 2:
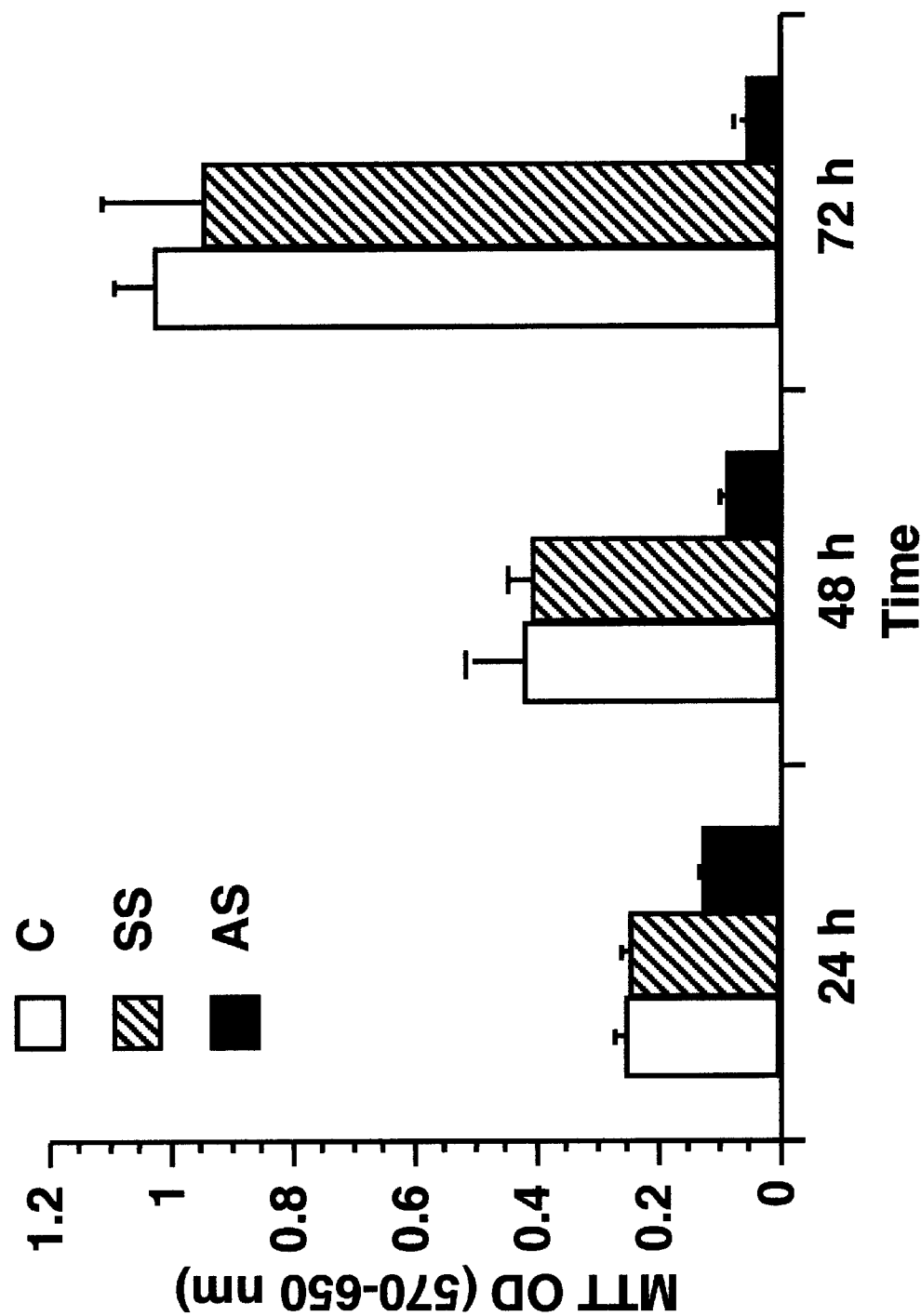
FIG. 2 is a graph illustrating inhibition of P12-L cell growth by Interleukin-10 antisense at various time points.

FIG. 2 is a graph illustrating inhibition of P12-L cell growth by IL-10 antisense at various time points. P12-L cells were cultured ($1\times10^4$ cell/well) in IMDM medium with 20 μM IL-10 antisense (ASI) or sense (SSI). Cells cultured in medium alone (CC) were also used as a control. Cells were cultured at 37° C. for different time intervals as indicated. MTT was added for another 4 hours. Afterwards, cultures were washed with PBS and blue formazon crystals were dissolved with 100% 2-propanol. ODs were read at 570 nm with 650 nm reference and background subtracted. The results are expressed as mean±SD of two individual experiments.

Figure 3:
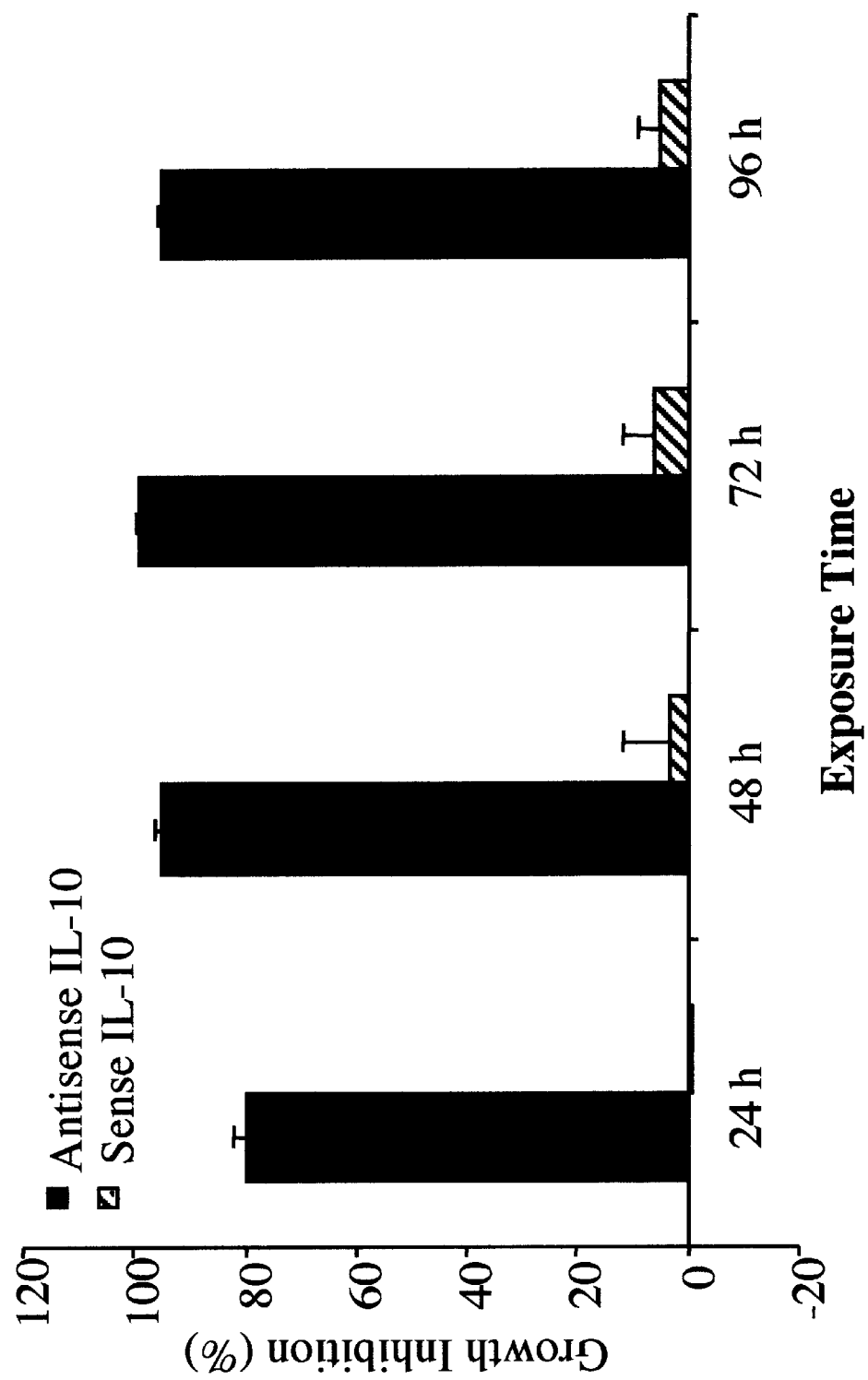
FIG. 3 is a graph illustrating the effect of antisense Interleukin-10 exposure time on growth inhibition.

FIG. 3 is a graph illustrating the effect of antisense IL-10 exposure time on growth inhibition. P12-L cells ($1\times10^4$ cells/well) were exposed to either 20 μM sense, antisense or media alone for 24, 48, or 72 hours. Following the specified exposure time the cells were washed and resuspended in fresh media. The MTT assay was performied at 96 hours for all groups. The results are expressed as % inhibition of MTT values of sense and antisense treated cultures relative to the appropriate media control MTT values. The results are expressed as mean±SD of two individual experiments.

Figure 4:
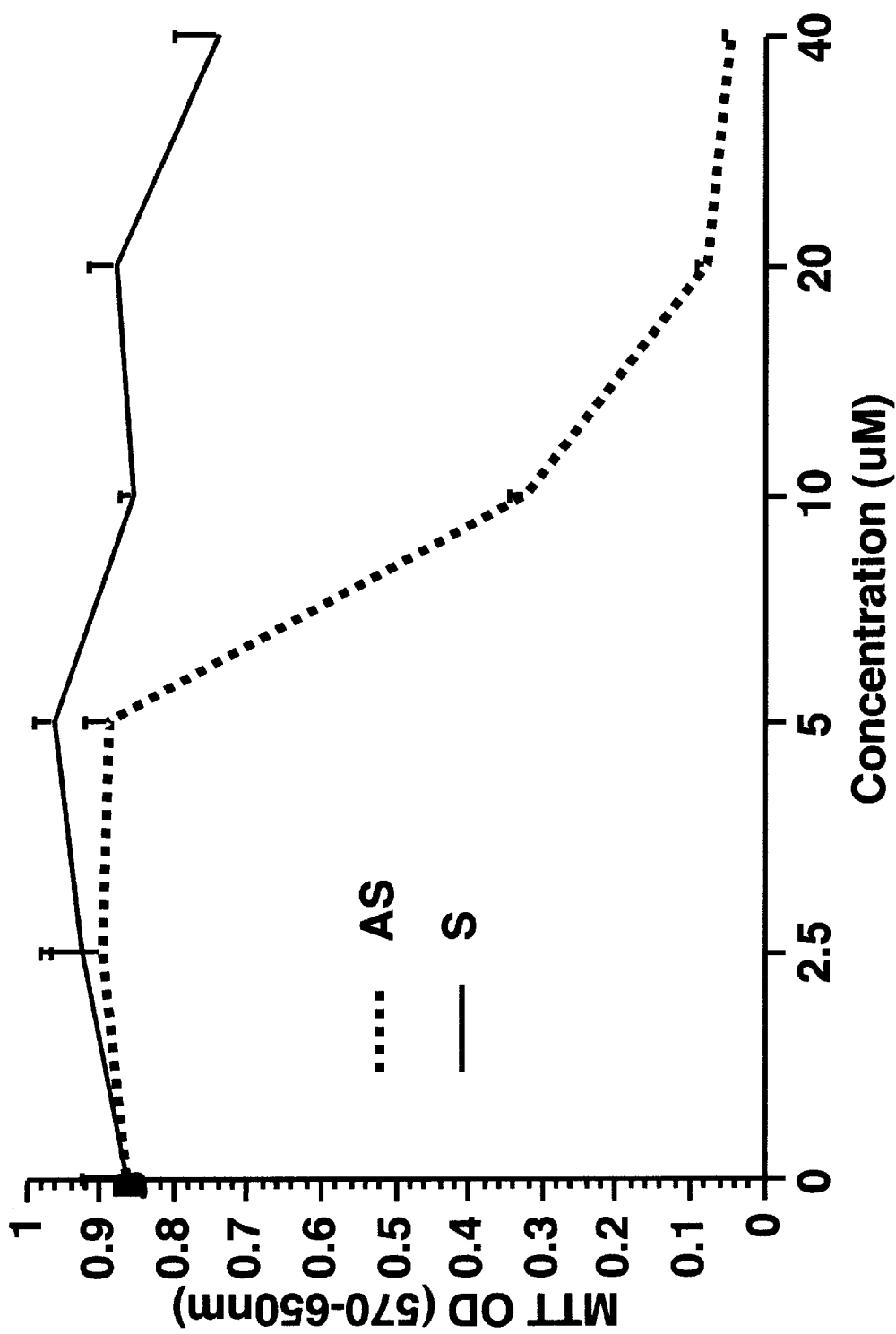
FIG. 4 is a graph illustrating the dose dependent effects of Interleukin-10 antisense.

FIG. 4 is a graph illustrating the dose dependent effects of IL-10 antisense. P12-L cells were cultured ($1\times10^4$ cell/well) in IMDM medium with different concentrations of IL-10 antisense (ASI) and sense (SSI) as indicated. Cells cultured in medium alone (CC) were also used as a control. After 72 hours of incubation at 37° C., MTT assay was performed as described above. The results are expressed as mean±SD of two individual experiments.

Figure 5:
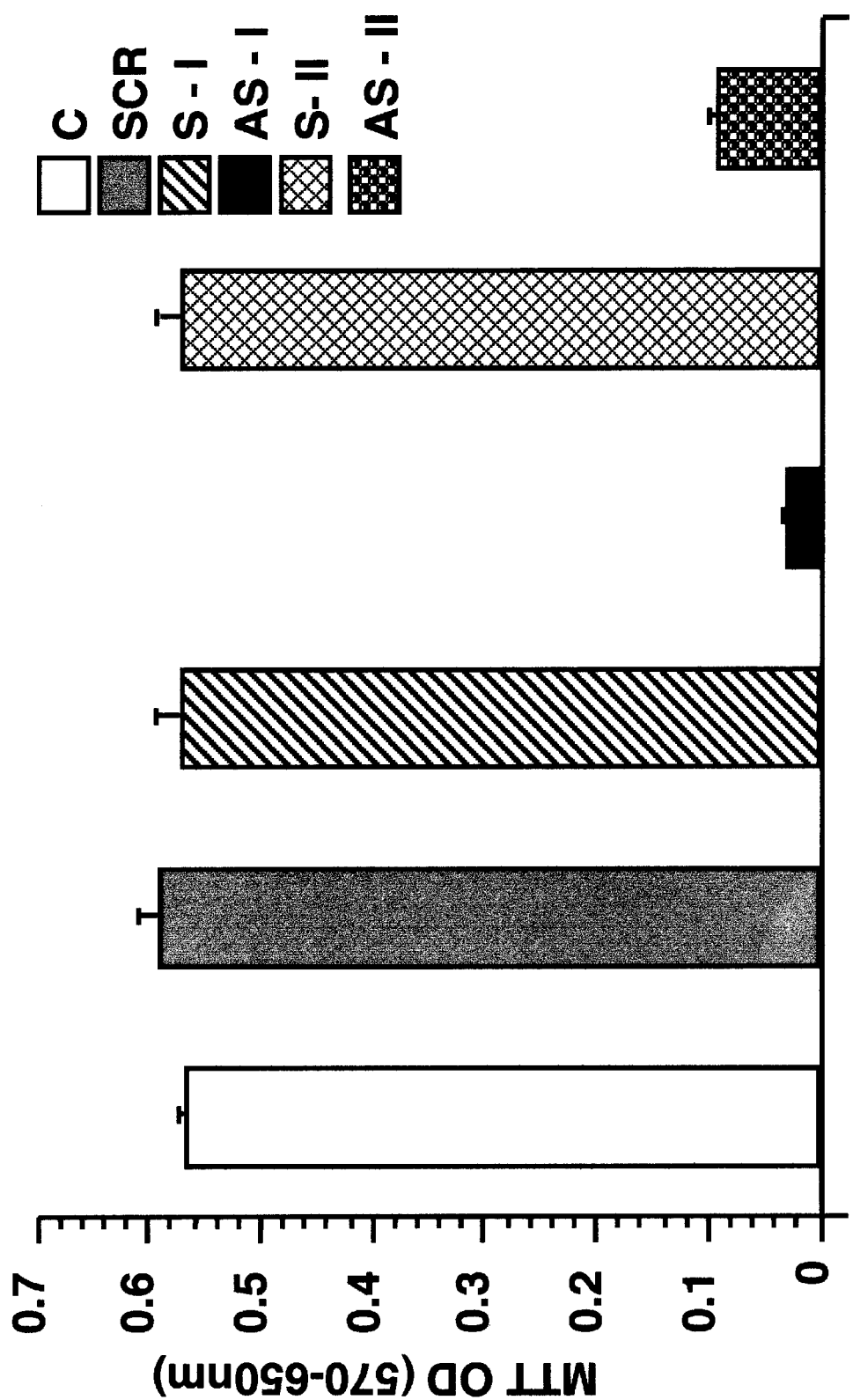
FIG. 5 is a graph illustrating the effect of different oligos on malignant B-1 cell growth.

FIG. 5 is a giraph illustrating the effect of different oligos on malignant B-1 cell growth. P12-L cells ($1\times10^4$ cells/well) were cultured with two antisense oligos (ASI, ASII) targeting at different regions of the IL-10 mRNA. As a control, medium alone and two corresponding sense oligos (SSI, SSII) and a scrambled oligo (SO) consisting of the same A,T,G,C content of ASI were employed. All oligos were used at 20 μM. After 72 hours, cell growth was measured by a MTT colorimetric assay. The results are expressed as mean±SD of two individual experiments.

Figure 6:
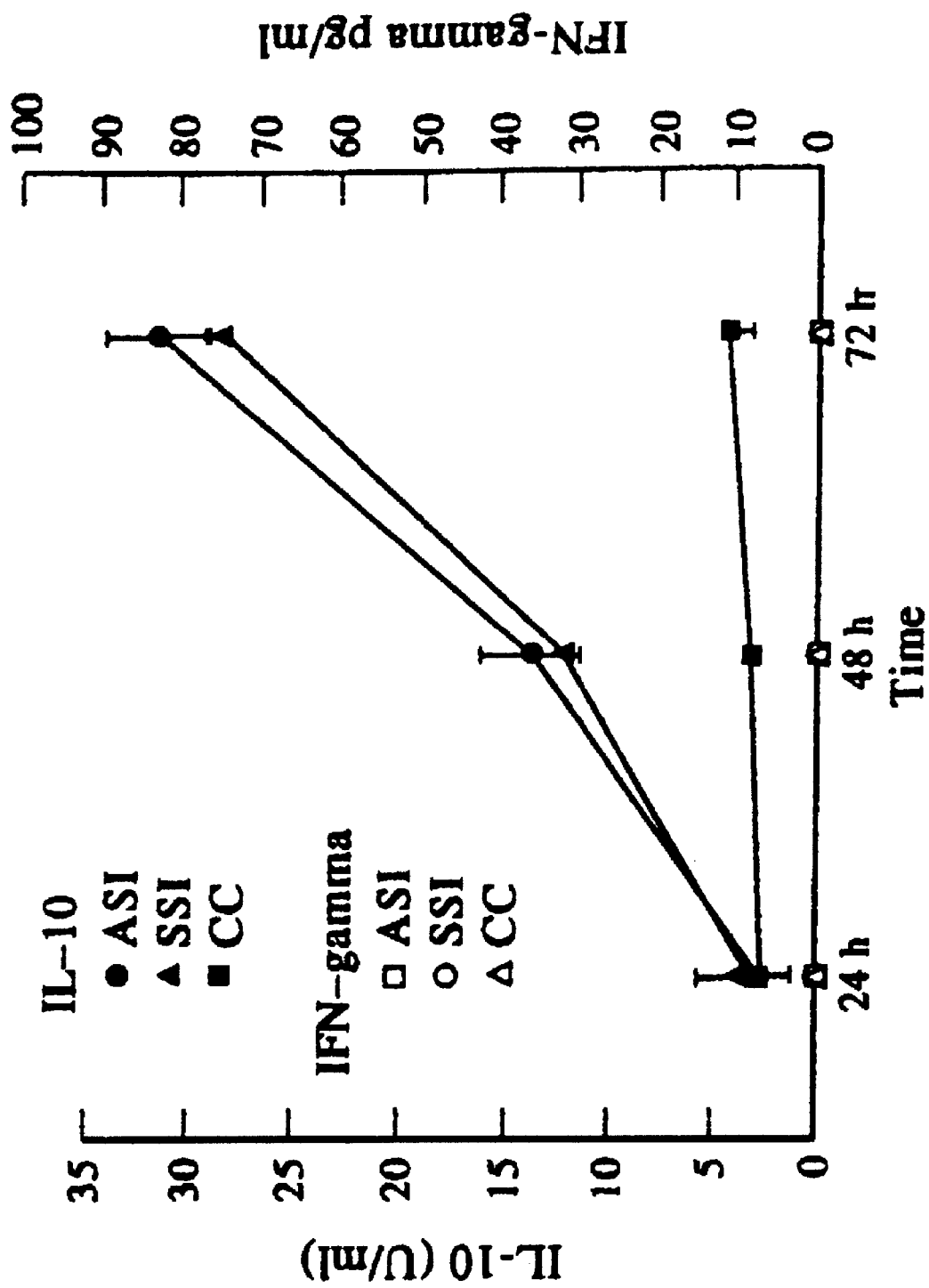
FIG. 6 is a graph illustrating the effects of antisense on Interleukin-10 and IFN-gamma secretion by P12-L.

FIG. 6 is a graph illustrating the effects of antisense on IL-10 and IFN-gamma secretion by P12-L. P12-L cells ($1 \times 10^4$ cell/ml) were incubated with 20 μM ASI, SSI or medium alone (CC) for 24, 48 and 72 hours. After each time interval, supernatants were collected, concentrated (5×) and measured for mIL-10 and IFN-gamma levels by murine IL-10 and IFN-gamma ELISA kits, as described above. The results are expressed as mean±SD of three individual experiments.

Figure 7A:
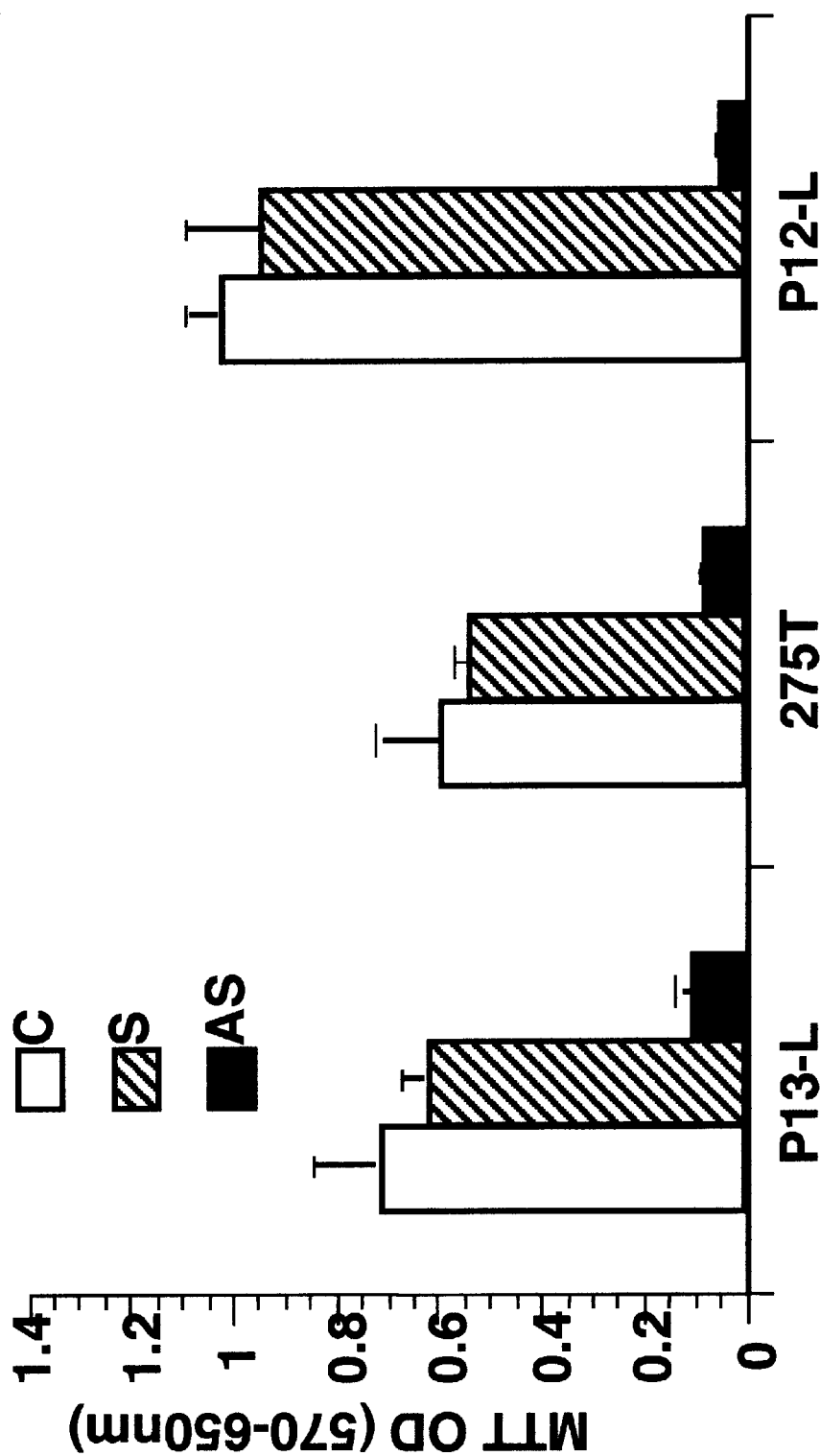
FIG. 7 is a graph illustrating the responses of different cell lines to Interleukin-10 antisense. Panel A (upper) consisted of three different malignant B-1 cell lines which possessed high levels of Interleukin-10 mRNA and required Interleukin-10 for growth. Panel B (lower) consisted of five different cell lines, some of which expressed Interleukin-10 message and some of which did not.
Figure 7B:
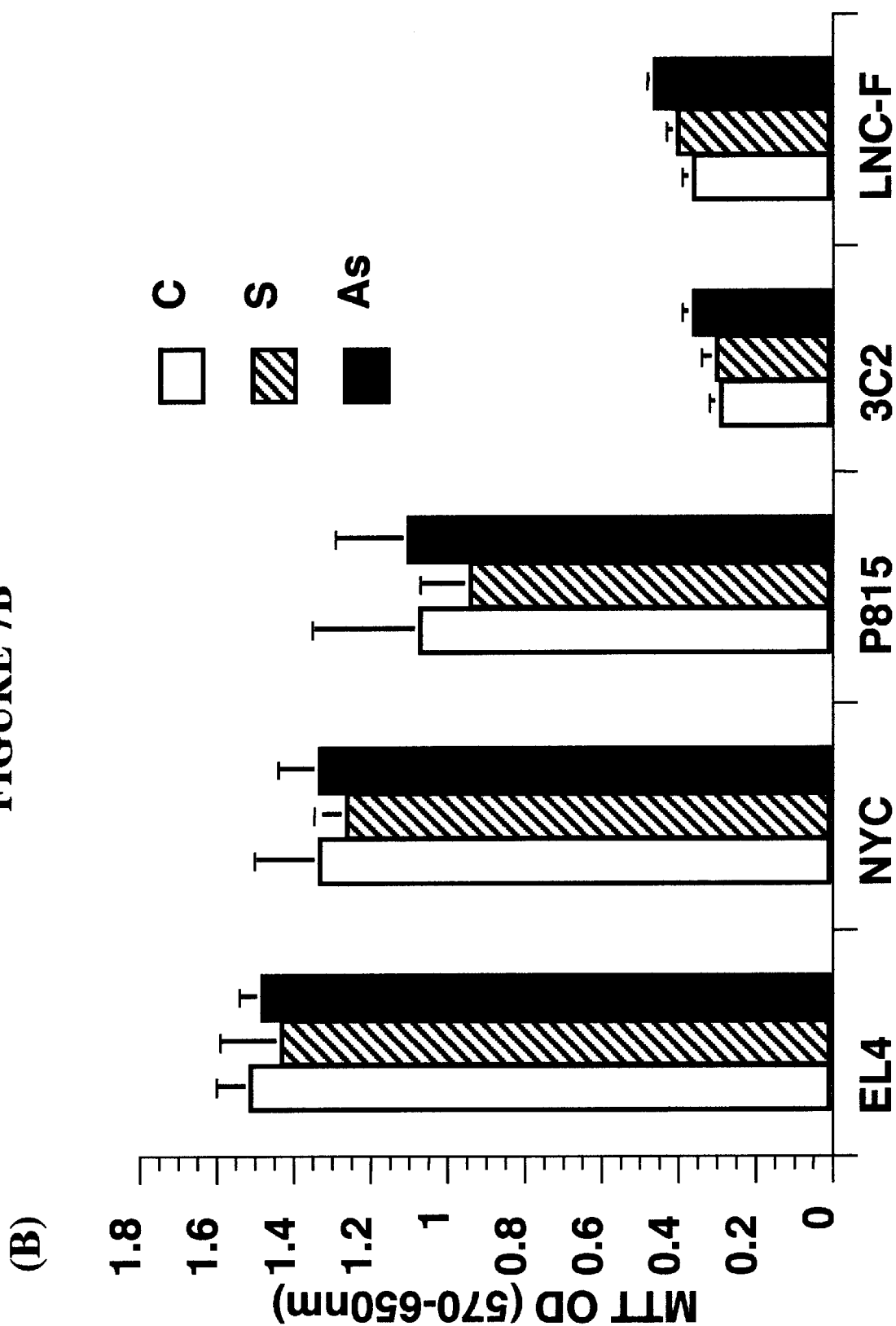

FIG. 7 is a graph illustrating the responses of different cell lines to IL-10 antisense. Different cell lines were cultured at $1 \times 10^4$ cell/well with 20 μM ASI, SSI or medium alone. After 72 hours of incubation at 37° C., MTT assay was performed as described above. Panel A (upper) consisted of three different malignant B-1 cell lines which possessed high levels of IL-10 mRNA and required IL-10 for growth. Panel B (lower) consisted of five different cell lines, some of which expressed IL-10 message and some of which did not. However, all of the cell lines in panel B did not recquire IL-10 for growth. The results are expressed as mean±SD of two individual experiments.

Figure 8:
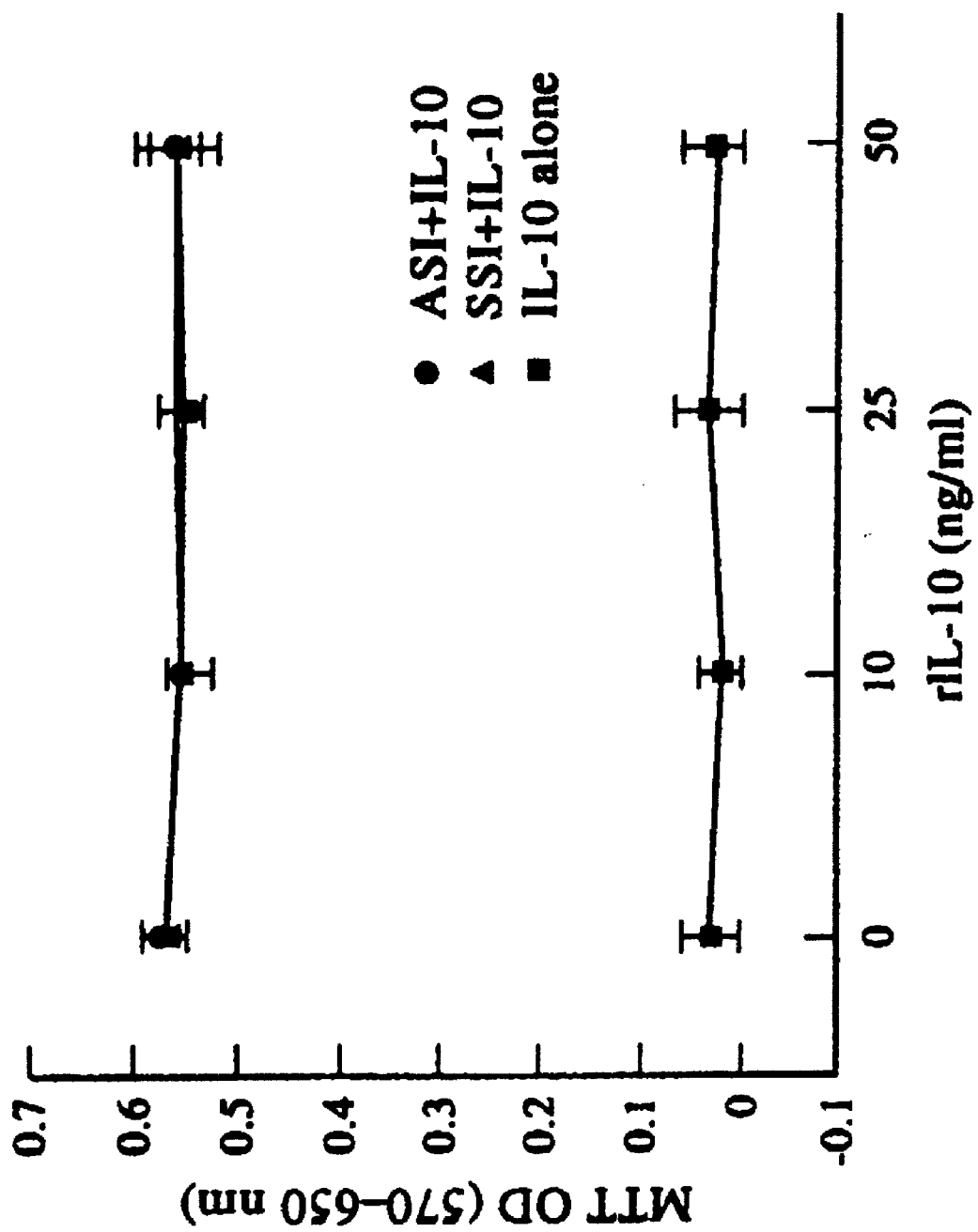
FIG. 8 is a graph illustrating the effects of rInterleukin-10 on malignant B-1 cell growth.

FIG. 8 is a graph illustrating the effects of rIL-10 on malignant B-1 cell growth. P12-L cells ($1 \times 10^4$ cells/well) were cultured with 20 μM ASI, SSI or medium alone and varying cencentrations of rIL-10 (0–50 ng/ml) for 72 hours. Afterwards, cell growth was measured using a MTT assay as described above. The results are expressed as mean±SD of two individual experiments.

Antisense Interleukin-10 ffects on Chronic Lymphocytic Leukeimia Cell Growth

Chronic Lymphocytic Leukeimia Cells:

Lymphocytes irom heparinized blood of human B-chronic lymphocytic leukemia patients or age-matched controls were obtained following Ficoll-Hypaque separation. In some cases B cells were further purified by depletion of monocytes by using L-leucine methyl ester (l-LME) and of T cells by rosetting with neuraminidase treated sheep red blood cells. Both before and after purification, samples that were tested, were stained with selected monoclonal antibodies, CD5 and CD19 (Caltag, San Francisco, Calif., USA) and analyzed by flow cytometric techniques on a FACscan (Becton Dickinson, Sunnyvale, Calif., USA). Cells ($5 \times 10^4$/well) were cultured in RPMI 1640 (GibcoBRL, Grand Island, N.Y., U.S.A.). All media was supplemented with 10% heat inactivated FBS (Hyclone, Logan, Utah, USA.) and 100U/ml penicillin/streptomycin.

Oligodeoxynucleotides:

The sequence of human IL-10 which used as the antisense oligo, was based on the a similar sequence successfully employed in the murine situation (51).

The IL-10 antisense oligos employed lack of homology to any other human gene sequences reported in the GEPN-BANK DNA database. The antisense/sense oligo pairs spanned regions close to the initiation site of IL-10 translation rather than the termination site (which occurs at residue 610). IL-10 antisense (AS) (5'-TGGGTCTTGGTTCTCAGCTTGGGGCAT) (SEQ ID NO: 1) and sense (SS) (5'-ATGCCCCAAGCTGAGAACAAGACCCA) (SEQ ID NO: 7) (regions 315–342) were thus chosen. All oligos were synthesized byi Operon Technologies Inc. (Alameda, Calif., USA). Oligos were diluted in medium and added at 20 μM concentrations at the beginning (time 0) of culture.

Exogenous Interleukin-10:

For the study of the effects of exogenous IL-10, recombinant hIL-10 (rIL-10) at 50 ng/ml and 100 ng/ml (Schering Plough, Kenilworth N.J., USA.) was added at time 0.

MTT Assay:

The MTT (3-(4,5-dimethylthiazol-2-yl)-2,5-diphenyl tetrazolium bromide) quantitative colorimetric assay was used to detect living, but not dead cells and the signal generated is dependent on the degree of activation of the cells. This can be used to measure cytotoxicity, proliferation or activation. In order to detect the cellular growth and survival, the MTT assay was performed according to published techniques with slight modifications (66). Briefly, cells ($5 \times 10^4$/well) were cultured with or without oligos for various times, then 20 μl of MTT (5 mg/ml in PBS, Sigma, St. Louis, Mo., USA) were added and the cells cultured at 37° C. for an additional 4 hours. The supernatants were gently flicked out and 150 μl of PBS were added and the plates were centrifuged for 5 minutes at 2000 rpm. After removal of PBS, 100 μl of 100% 2-propanol were added and vigorously pipetted to dissolve the formazan crystals. Plates were stored in dark for 30 minutes at room temperature and read at 570 nm with a reference at 650 nm on a Kinetic Microplate reader (Molecular Devices, Menlo Park, Calif., USA). Optical density (OD) was determined and background values subtracted.

Quantification of Cytokine Message Levels by PCR Analysis:

Total RNA was prepared using RNAzol B according to the manufacturer's specifications (TEL-Test, Friendswood, Tex., USA). Reverse transcription and PCR were performed according to the manufacturer's instructions included with the Perkin Elmer Cetus GeneAmp RNA PCR kit (Perkin Elmer Cetus Corp., Norwalk, Conn., USA). All primers and probes were synthesized by Operon Technologies Inc. (Alameda, Calif., USA). IL-10 and b-actin primers employed have previously been described (53, 67). PCR sample quality was examined on a 2% NuSieve agarose gel (FMC Eiioproducts, Rockland, Me., USA) using ethidium bromide and analyzed using ImageQuant software (Molecular Dynamics, San Francisco, Calif., U.S.A.). The densitometric values for the IL-10 PCR products are expressed as the ratio of IL-10 PCR product/b-actin PCR product in order to normalize for the amount of RNA present in each sample.

Anti-IgM Treatment of Cultures:

In order to incLuce apoptosis and reduce viability by a method independent of antisense IL-10, separate cultures were exposed from time 0 with anti-IgM at 8 μg/ml (Sigma).

FIG. 9 is a graph illustrating flow cytometric analysis of cells obtained from the peripheral blood of a patient with B-chronic lymphocytic leukemia. Histograms represent profiles obtained following dual color staining of cells with anti-CD19 FITC and anti-CD5 PE. Panel B (upper) is a contour plot of unpurified PBL. Panel B (lower) is obtained following purification of B cells as described above.

FIG. 10 is a graph illustrating representative data on growth inhibition following culturing of the PBL from an individual B-chronic lymphocytic leukemia patient. MTT assay was performed at 24, 48 and 72 hours. The results are expressed as % inhibition of MTT values of anti-IgM, sense IL-10 and antisense IL-10 treated cultures relative to the appropriate media control MTT values. The results are expressed as mean±SD.

Figure 11:
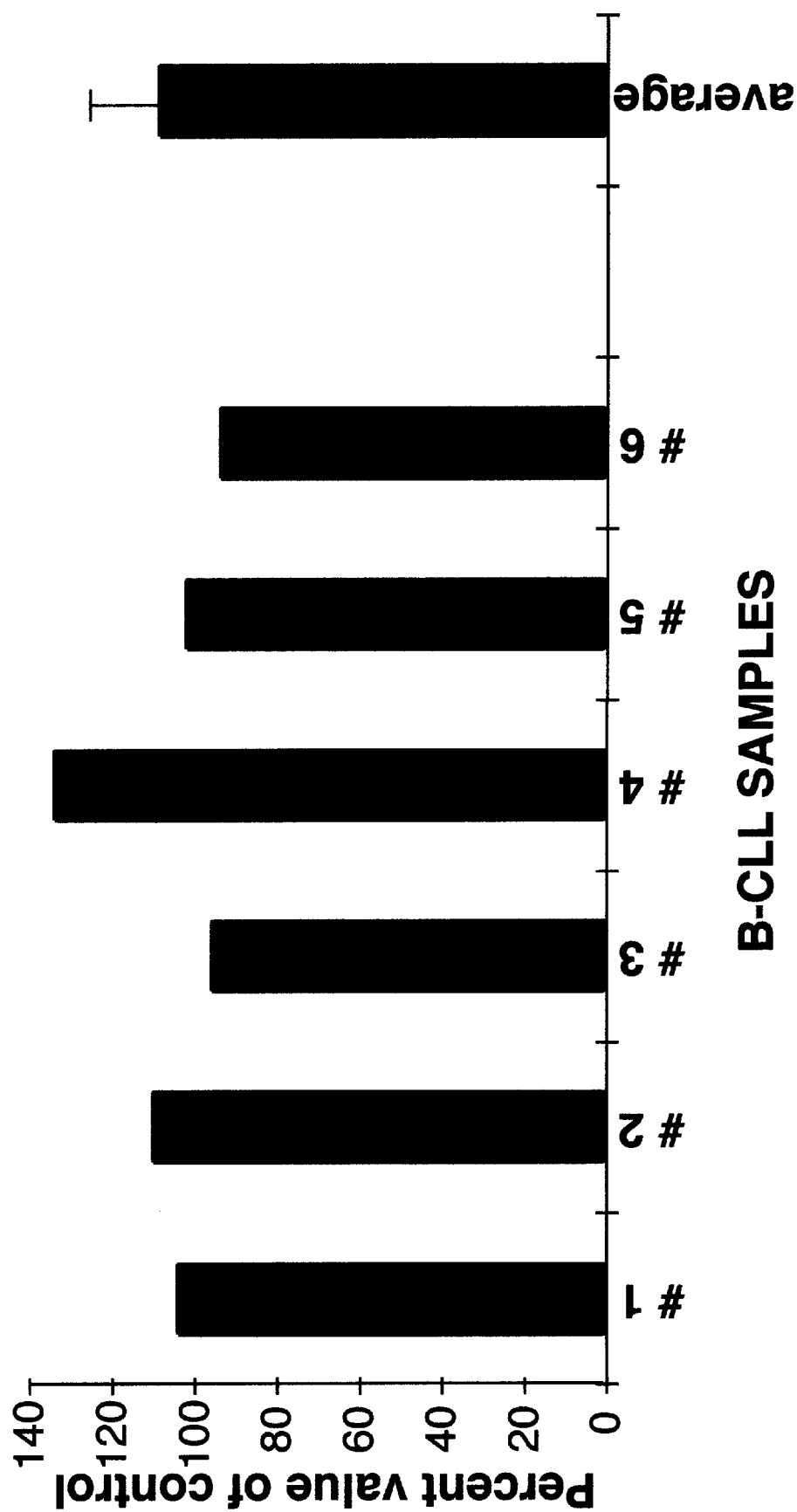
FIG. 11 is a graph illustrating the effect of exogenous addition of Interleukin-10 on the growth ol malignant B-chronic lymphocytic leukemia cells.

FIG. 11 is a graph illustrating the effect of exogenous addition of IL-10 on the growth of malignant B-chronic lymphocytic leukemia cells. All chronic lymphocytic leukemia cells were cultured in the presence of 100 ng/ml of IL-10. After 72 hours of incubation at 37° C., MTT assay was performed as described above. The results are expressed as mean±SEM.

FIG. 12 is a graph illustrating the correlation between IL-10 message levels (expressed as densitometric PCR values normalized to the expression of the housekeeping gene) and inhibition by antisense IL-10 (expressed as control MTT values minus experimental) (panel A, upper) or the presence of CD5 +B cells as determined by flow cyotmetric analysis (panel B, lower) in individual chronic lymphocytic leukemia samples.

In Vivo Antisense IL-10 Prevents Expansion of a B-1 Leukemia/Lymphoma

Cells Lines: NZB Derived Malignant B-1 Cells:

P12-L is an aggressive malignant B-1 cell line derived from NZB mice and serves as an in vitro leukemic cell line (6) P12-L has been carried in vitro for over two years in Iscole's modified Dulbecco's medium (IMDM) from GibcoBRL, Grand Island. All media was supplemented with 10% heat inactivated FBS (Hyclone, Logan, Utah, USA.) and 100 U/ml penicillin/streptomycin.

Oligonucleotides (Oligos):

Based on the reported sequence of murine IL-10 (90) several antisense oligos were employed. IL-10 antisense I (ASI) and sense I (SSI) are the same sequences as previously reported (91). The IL-10 antisense oligos employed were chosen because they had a lack of homology to any other murine gene sequences reported in the GENBANK DNA database. The antisense/sense oligo pairs spanned regions close to the initiation site of IL-10 translation rather than the termination site (which occurs at residue 610). IL-10 antisense I (ASI) (5'-CATTTCCGATAAGGCTTGCG) and sense I (SSI) (5'-CCAAGCCTTATCGGAAATG) (regions 315–333); and a scrambled oligo (SO), (5'-TTTATTGCGCACGACGGAT) which has the same base content of IL-10 ASI were used. In the case of delivery of oligos via the mini-osmotic pumps, the oligonucleotdies were employed as phosphorothioate derivatized preparations.

In Vitro Treatment with Oligos:

To determine if antisense IL-10 induced apoptosis in cultured malignant B-1 cells, the P12-L NZB malignant B-1 cell line was cultured for various times post addition of antisens or sense oligos to the culture media as previously described (91). The cells were analyzed for growth inhibition by an MTT assay (91) or for the induction of apoptosis by detection of a sub-G1 peak as previously described (92).

In Vivo Delivery of Oligos:

All mice were (NZB×DBA/2) F1 mice (between the ages of 2–10 months) which received iv transfer of $10 \times 10^6$ cells from the P-12L malignant line of NZB derived B-1 cells. At the time of transfer of the malignant cells, the mice also received the antisense oligonucleotides. Control animals were either (NZB×DBA/2)F1 animals receiving the malignant cells and the sense oligo, F1 animals receiving the malignant cells and the scramble antisense, or F1 animals receiving the malignant cells and the vehicle alone (either pump or cochleate). Not all controls were employed in each experiment. Two methods for delivering oligonucleotides in vivo were employed, mini-osmotic pumps or lipid vesicles (cochleates).

Osmotic Pumps:

Osmotic pumps (Alza, Palo Alto, Calif.) model 2002 (delivering 0.5 ul/hr) were employed in Experiment 1 and 2. The pumps have a maximum volume of 2 ml, which necessitated that the model 2002 be removed and a new pump reimplanted on Day 14. The usual dose received for the 28 days of infusion was 300 ug/day. In the dosing experiment three doses were employed (30 ug, 100 ug, and 300 ug/day).

Cochleate:

The exact procedure for formulating the cochleates has previously been described (93). The overall procedure is that the oligonucleotides are added to dried down phosphatidylserine and cholesterol. Calcium is added, resulting in the formation of long sheets of calcium-chelated phospholipid bilayers. These then roll up to form cochleate cylinders which are solid precipitates containing entrapped oligonucleotides with no internal aqueous space. The final concentration of oligonucleotide is 2500 ug/ml and the final concentration of calcium is 6 mM. The mice are injected iv on Day 0 and Day 5 with 0.2 ml (500 ug). The cochleates are diluted further to deliver 250 ug on Day 8 and 85 ug on Day 14 for a total of 1.3 mg. Control mice receive the same amount of cochleate alone. It is hypothesized that contact of the calcium-rich highly ordered membrane of the cochleate with a cell results in a perturbation and reordering of the cell membrane which results in a fusion event and delivery of a small amount of oligonucleotide into the cytoplasm. The cochleate may then still be able to break free and be available for another fusion event with the same or another cell (94).

Flow Cytometric Analysis of Transferred Malignant B-1 Cells:

Cells ($1 \times 10^6$) were obtained from tissue and were stained with the following reagents: FITC conjugated goat anti-mouse IgM, anti-CD5 or anti-B220 conjugated with phycoerythrin (PE) (Caltag, San Francisco, Calif.). Isotypic antibodies were employed as controls to set the quadrants. Cells were analyzed on a FACScan flow cytometer using Lysis II software (Becton Dickinson, Sunnyvale, Calif.). For cell cycle analysis, cell suspensions were fixed in cold 70% ethanol followed by staining with propidium iodide (PI, 50 ug/ml, Calbiochem) and ribonuclease (1 mg/ml, Perkin-Elmer) for 30 min at 37° C. In all cases 20,000 events were analyzed.

Histopathologic Examination of Recipient Mice:

Liver, spleen and lymph node were fixed in 10% formalin solution, embedded in paraffin, and cut into 6-um sections. The brain, bone marrow, and spinal cord were fixed in 10% formalin and then decalcified with diluted nitric acid, embedded in paraffin and cut in to 6 um sections. Section were stained with hematoxylin-eosin (H&E) and examined by light microscopy.

Results

Growth Inhibition of Malignant CD5+B (B-1) Cells by Antisense Interleukin-10

Quantification of mIL-10 mRNA by RT-PCR of Various Cell Lines

An RT-PCR method was employed to detect the mIL-10 mRNA present in various cell lines studied. This technique is semiquantitative and primers specific for the housekeeping gene, HPRT, are employed to verify that approximately the same amount of RNA is subjected to RT/PCR in all the samples analyzed. As shown in FIG. 1, 3C2, P815, and EL-4 showed no detectable IL-10 mRNA while NYC and LNC-F showed a low and moderate IL-10 mRNA level respectively. IL-10 is not a growth factor for all the cell lines mentioned above. In contrast, malignant B-1 cells (P12-L and P13-L) not only required IL-10 as a growth factor, but also possessed high levels of IL-10 mRNA. This unique characteristic formed the basis of IL-10 antisense therapy for malignant B-1 cells.

Growth Inhibition Effect of Interleukin-10 Antisense

The NZB derived malignant B-1 cell line, P12-L was found to possess high levels of IL-10 mRNA (6). For the study of growth regulation, this cell line was studied for the effect of IL-10 antisense on the growth inhibition. The results (FIG. 2) demonstrated that the growth of the malignant B-1 cell line, P12-L, is significantly inhibited by IL-10 antisense oligodeoxynucleotides (IL-10 ASI). The inhibition rates are 49.6%, 80.1%, 94.9% at 24, 48, and 72 hours, respectively. The maximal inhibitory effect of IL-10 antisense was achieved at 72 hours. Contrary to the antiserse treatment group, the sense and control treatment groups showed a steady rise in cell number as the time intervals increased from 24 to 72 hours. Similar results were obtained for P12-L cells cultured in the presence of 20 $\mu$M IL-10 antisense for longer periods of time, 4 days and 7 days. Greater than 95% reduction in MTT was observed at these later time points when compared to media control. In contrast, no difference was observed between media control and sense treated cultures at these later time points. Trypan blue exclusion studies indicated that in cultures treated with antisense IL-10, by Day 4 greater than 95% of the cells took up the dye. Likewise on Day 7, more than 95% of the cells were dead following IL-10 antisense treatment.

Analysis by light microscopy indicated that the few remaining viable cells following IL-10 antisense treatment were exclusively slow-dividing stromal cells in contrast to the sense treated wells in which the rapidly dividing P12-L cells were the majority of viable cells. Electron micrographs of P12-L cells (data not shown) at 48 hours post-antisense treatment confirmed that most of the remaining viable cells had stromal cell morphology and the dead lymphoid cells had apoptotic features.

Additional experiments were performed to determine the minimal amount of time cells must be erlposed to antisense in order to result in inhibition of growth. Washout experiments were performed in which P12-L cells were exposed to either antisense, sense or media alone for a specified time (FIG. 3). The cells were then washed and re-cultured in fresh media for a total of 96 hours of culture. Even following only 24 hours of initial exposure to antisense IL-10, significant growth inhibition was observed at the 96 hour assay time point. There was little difference observed between cells cultured in the presence of IL-10 antisense for only 48 hours and those cells e)iposed to antisense for the entire culture period.

Dose Dependence of Interleukin-10 Antisense

Due to the limited cell uptake and the rapid degradation of oligos, a sufficient dose of oligos would be required. As shown in FIG. 4, IL-10 antisense inhibited the growth of P12-L cells in a dose dependent manner. As the IL-10 antisense oligo concentrations increased from 5 to 40 $\mu$M, the inhibitory effect increase rapidly, and maximal inhibitory effect of antisense oligo was observed at 40 $\mu$M. Concentrations less than 5 $\mu$M of antisense showed no notable effects. On the other hand, the corresponding sense oligo showed no significant effects on P12-L cell growth at all concentrations.

Effects of Different Oligodeoxynucleotides Derived from the Interleukin-10 sense or Antisense Sequence In order to determine the specificity of the inhibitory effect of IL-10 antisense, several different olig,ros were employed. As shown in FIG. 5, another IL-10 antisense (ASII, closer to the 5' region than ASI) showed similar inhibitory effects. The corresponding sense oligo (SSII) had no effects on malignant B-1 cell growth as had previously been observed for SSI. A scrambled oligo consisting of the same A,T,G,C content of ASI was also employed. In contrast to the antisense oligo, the scrambled oligo shovved no inhibitory effect on the growth of malignant B-1 cells.

Effects of Interleukin-10 Antisense on the Production of Interleukin-10 and IFN-gamma The P12-L cell line has been extensively analyzed (6). Since P12-L cells express high levels of IL-10 mRNA and are exquisitely sensitive to IL-10 antisense treatment, the cytokine protein levels were studied in this line. P12-L cells can spontaneously secrete IL-10. Upon the IL-10 antisense entry into the cells, IL-10 translation is expected to be interrupted. The secretion of IL-10 in antisense treated and untreated groups was measured by ELISA. As shown in FIG. 6, the IL-10 in the supernatants of the antisense treated group remained at the background level, while the IL-10 in both the sense treated group and the control group increased markedly with time in culture. The IL-10 levels of both sense and control groups were similar. Since human chronic lymphocytic leukemia cells have been reported to produce IFN-gamma (31) and IL-10 can inhibit the production of IFN-g (32), the e-ffects of IL-10 antisense treatment on the malignant cells in terms of the production of IFN-gamma was investigated. The levels of IFN-gamma in the supernatants of IL-10 antisense treated cell cultures were assayed. No increase of IFN-gamma in culture supernatants of antisense treated or sense treated group was detected. None of the concentrated culture supernatants (antisense treated, sense treated and control) showed detectable levels of IFN-gammma (FIG. 6).

Effects of Interleukin-10 Antisense on Various Cell Lines

The inhibitory effects of IL-10 antisense oligos were not observed in all cell lines studied. Individual cell lines displayed different responses to IL-10 antisense (FIG. 7). The growth of those malignant B-1 cell lines (P12-L, P13-L, 275T) which possessed elevated levels of IL-10 mRNA were significantly inhibited in the presence of IL-10 antisense. There is a significant growth inhibition effect when compared to the growth of sense oligo treated and medium control groups. In contrast, the growth of the control cell lines (EL-4, NYC, P815, 3C2 and LNC-F) was not affected by IL-10 antisense. No significant differences among the control cell lines was noted between the antisense, sense, and medium groups. For all the control cell lines, IL-10 is not a required growth factor, although some of the control lines possessed IL-10 mRNA (FIG. 1).

Failure to Reverse Inhibitory Effect of Interleukin-10 Antisense by the Addition of Exogenous Interleukin-10

If IL-10 is an atitocrine growth factor for malignant B-1 cells, it is reasonable to postulate that addition of exogenous IL-10 should enhance the growth of these cells and reverse the inhibitory effect of IL-10 antisense. However, in our experiments the addition of rIL-10 neither enhanced the growth of malignant B-1 cells, nor reversed the growth inhibitory effect of IL-10 antisense, even at high concentrations up to 50 ng/ml (25 fold higher than physiological IL-10 levels) (FIG. 8).

Antisense Interleukin-10 Effects on Chronic Lymphocytic Leukemia Cell Growth

Surface Expression of CD5 on Chronic Lymphocytic Leukemia Cells:

Dual staining inalysis of PBL from an individual B-chronic lymphocytic leukemia patient is shown in FIG. 9. This patient had a population of homogeneously staining cells which were CD19+ and expressed low levels of CD5 (FIG. 9A). On further purification the cells were found to be exclusively CD5+B cells with <1% residual T cells (FIG. 9B). The proportion of CD5+B cells in the PBL varied in the six patients studied from 20–87%.

Growth Inhibitory Effect of Interleukin-10 Antisense:

Six chronic lymphocytic leukemia samples were cultured for three days in complete medium with either no additives or 20 μM sense IL-10, 20 μM antisense oligonucleotides or 8 μg anti-IgM. At intervals of 24, 48 and 72 hours, the cells were assayed for vialbility by the MTT assay (Table 1). Anti-IgM was employed as a known agent which induces apoptosis in malignant B-1 cells (68, 69). Sense IL-10 oligodeoxynucleotides did not have any significant effect on the viability of the cells when compared to cultures in which no additives were employed (control). In contrast, at 72 hours, the antisense IL-10 showed significant inhibition of viability in 3/6 patients studied. The inhibitory effect of antisense IL-10 was observed to occur in a time dependent manner as seen in a representative sample (FIG. 10). The maximal inhibitory effects of IL-10 antisense and anti-IgM were achieved at 72 hours. Contrary to the antisense treatment group, the sense treatment group showed a steady rise in cell number as the time intervals increased from 24 to 72 hours. Control PBL from age-matched non-chronic lymphocytic leukemia normals showed no growth inhibition by any of the additives employed. Unfortunately, it iwas impossible to obtain enough purified CD5+B cells from normal PBL to absolutely determine that antisense-IL-10 had no inhibitory effect on B-1 cells. Flowever, based on the results using unpurified PBL in non-chronic lymphocytic leukemia controls, antisense IL-10 and anti-IgM had no inhibitory effects. The overall effects of antisense IL-10, sense IL-10 and anti-IgM are summarized in Table 1.

TABLE 1

Effect of Antisense Interleukin-10 on B-Chronic Lymphocytic Leukemia Cells

| Effects of | Sense | Antisense IL-10 | Anti IgM |
|---|---|---|---|
|  | 88* | 36 | 41 |
|  | 109 | 84 | 23 |
|  | 115 | 83 | 64 |
|  | 103 | 116 | 56 |
|  | 93 | 101 | 72 |
| Average | 101.6 | 84 | 51.2 |
| St. Dev. | 11.6 | 30.1 | 19.4 |

*Results are expressed as percentages of control values.

Effect of Exogenous Interleukin-10:

Previous investigators have reported that IL-10 itself can be inhibitory for malignant B-1 cells (70). However, in our experiments the addition of rIL-10 neither enhanced nor inhibited the growth of malignant B-1 cells (FIG. 11).

Figure 12A:
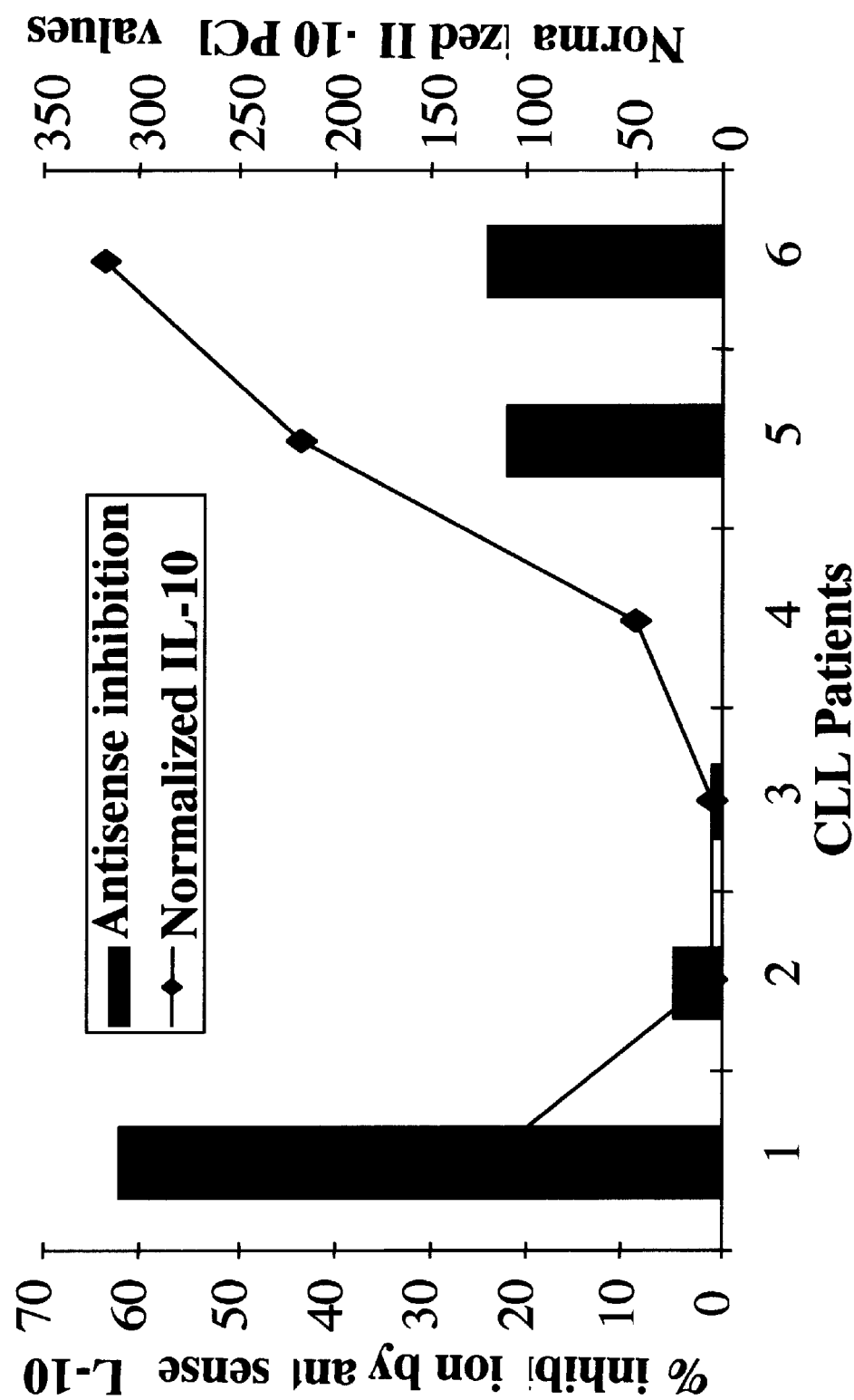
FIG. 12 is a graph illustrating the correlation between Interleukin-10 message levels (expressed as densitometric PCR values normalized to the expression of the housekeeping gene) and inhibition by antisense Interleukin-10 (expressed as control MTT values minus experimental) (panel A, upper) or the presence of CD5+B cells as determined by flow cyotmetric analysis (panel B, lower) in individual chronic lymphocytic leukemia samples.
Figure 12B:
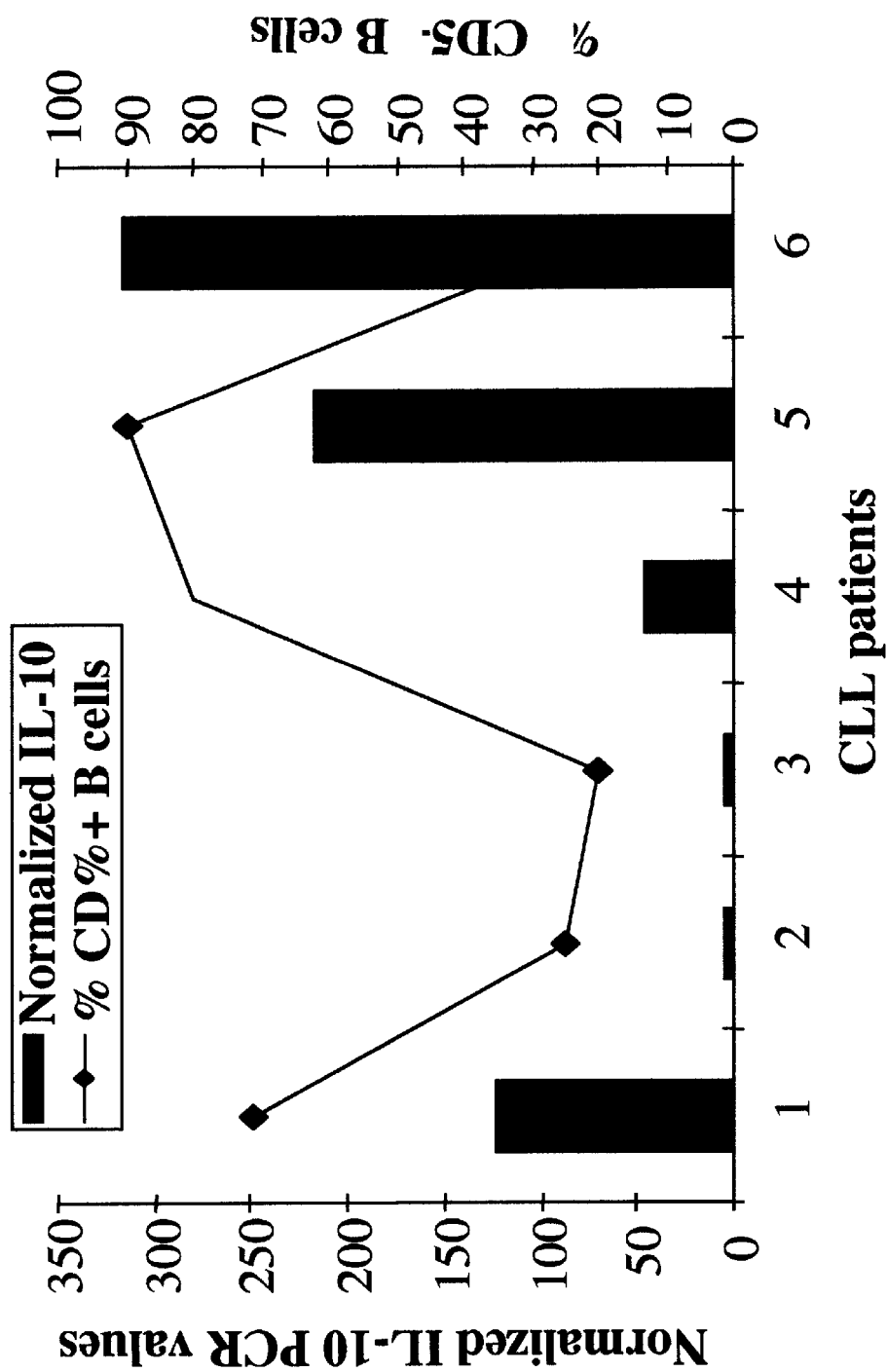

Quantification of Interleukin-10 mRNA by RT-PCR:

An RT-PCR method was employed to detect the IL-10 mRNA present in various B-chronic lymphocytic leukemia samples. This technique is semiquantitative and primers specific for the housekeeping gene, b-actin, are employed to verify that approximately the same amount of RNA is subjected to RT/PCR in all the samples analyzed. The growth inhibitory effect of antisense IL-10 was directly related to the presence of detectable levels of IL-10 mRNA (FIG. 12A). In the absence of IL-10 mRNA expression, antisense IL-10 was ineffective. However, there was no significant correlation between the levels of CD5+B cells in the patients and the levels of IL-10 mRNA (FIG. 12B).

In Vivo Antisense IL-10 Prevents Expansion of a B-1 Leukemia/Lymphoma

In vitro Analysis of Apoptosis Induced by Antisense IL-10:

IL-10 has been shown to inhibit the in vitro growth of malignant B-1 cells in a time and dose dependent manner (91). In FIG. 13 the ability of antisense IL-10 to induce apoptosis as detected by an increase in cells with sub-G1 DNA content was observed. As early as 24 hours post treatment an increase in apoptotic cells was observed in the antisense IL-10 treated malignant B-1 cells. This increase continued at 48 hours. The increase in apoptotic cells correlated with the growth inhibition measured by the MTT assay. The fact that antisense IL-10 appeared to induce apoptosis in the malignant B-1 clones suggested that in vivo treatment of mice expanding a population of malignant B-1 cells might also induce apoptosis and prevent the leukemia/lymphoma from killing the recipient animal.

Figure 14:
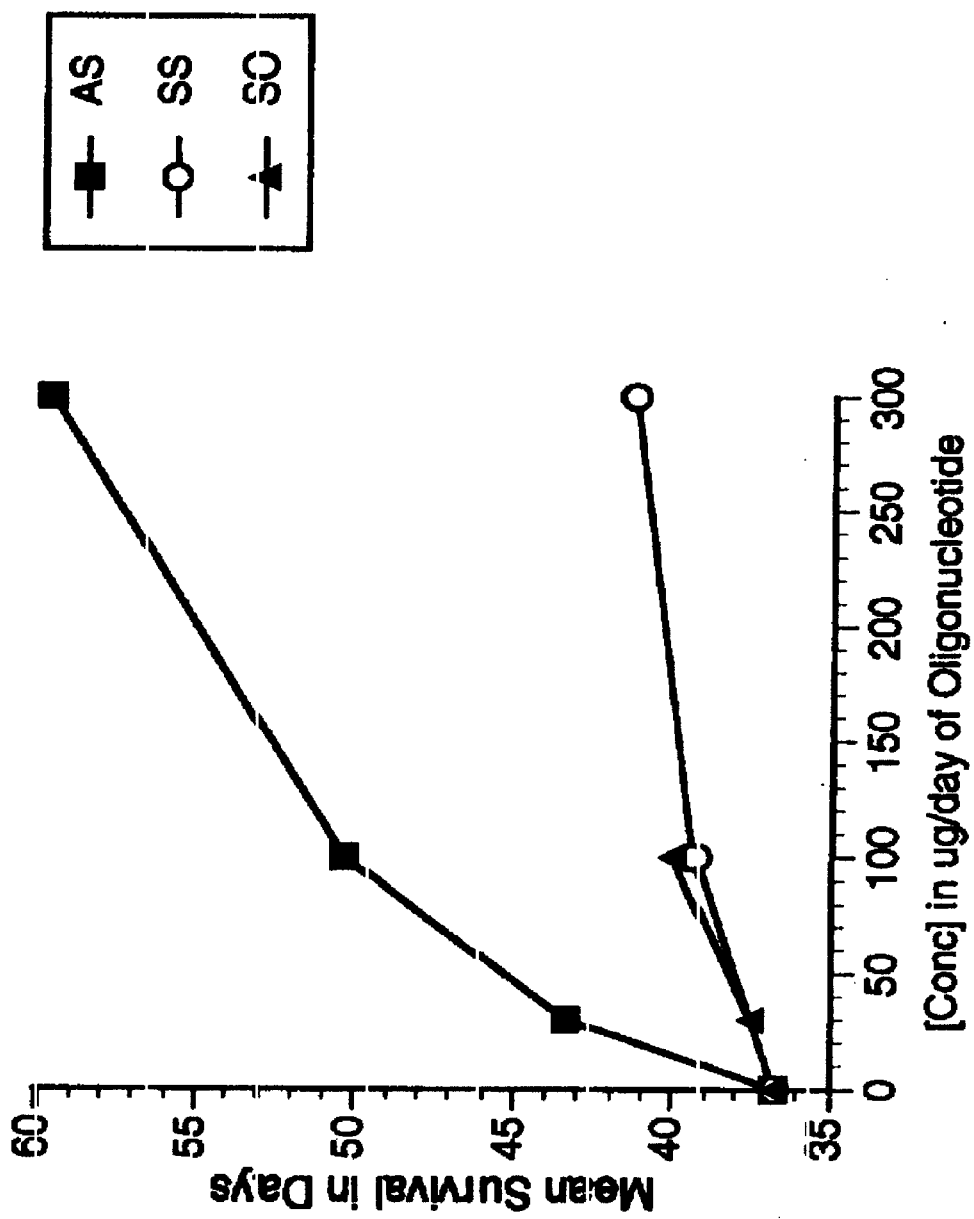
FIG. 14 is a graph showing that mice (NZB×DBA/2)F recipients which received 10×10$^6$ malignant B-1 cells and the mean survival in days for each group at the various concentrations is shown.

Treatment of Animals with Constant Infusion of Phosphorothioate Modified Oligonucleotides:

Recipient (NZB×DBA/2)F1 animals were transferred with malignant B-1 cells and implanted with mini-osmotic pumps to deliver the phosphorothioate oligonucleotides. Because the small pumps only have enough volume to deliver oligo for 14 days, they are removed and replaced with fresh pumps on day 14. The total time of constant infusion is therefore 28 days. In the first experiment, mice were divided into groups and implanted sc with pumps containing either antisense IL-10 (AS), sense (SS) or control scrambled oligos (SO). In order to determine the mosi effective dose to deliver, groups were subdivided (3 mice/subgroup) and three doses were employed (30 ug/day, 100 ug/day and 300 ug/day). The transferred malignant B-1 cells were hyperdiploid, CD5+ B220−, IgM+ cells and could readily be distinguished from either normal B cells or non-malignant B-1 cells. Recipient of the leukemic cell line die due to expansion of the malignant B-1 cells in both lyraphoid and non-lymphoid tissues. The animals near the end-point of survival demonstrate a characteristic hind-leg paralysis as previously described (6). The mean survival for this initial experiment at the various doses of oligonucleotide is shown in FIG. 14. Using the phosphorothioate oligonucleotides at a constant rate of infusion for 28 days the highest survival rate was seen in the group of animals receiving the antisense IL-10. The mean survival was increased in antisense IL-10 treated animals in a dose dependent manner. Because the survival was varied in the antisense treated group, the highest dose (300 ug/day) was chosen for further study.

Figure 15A:
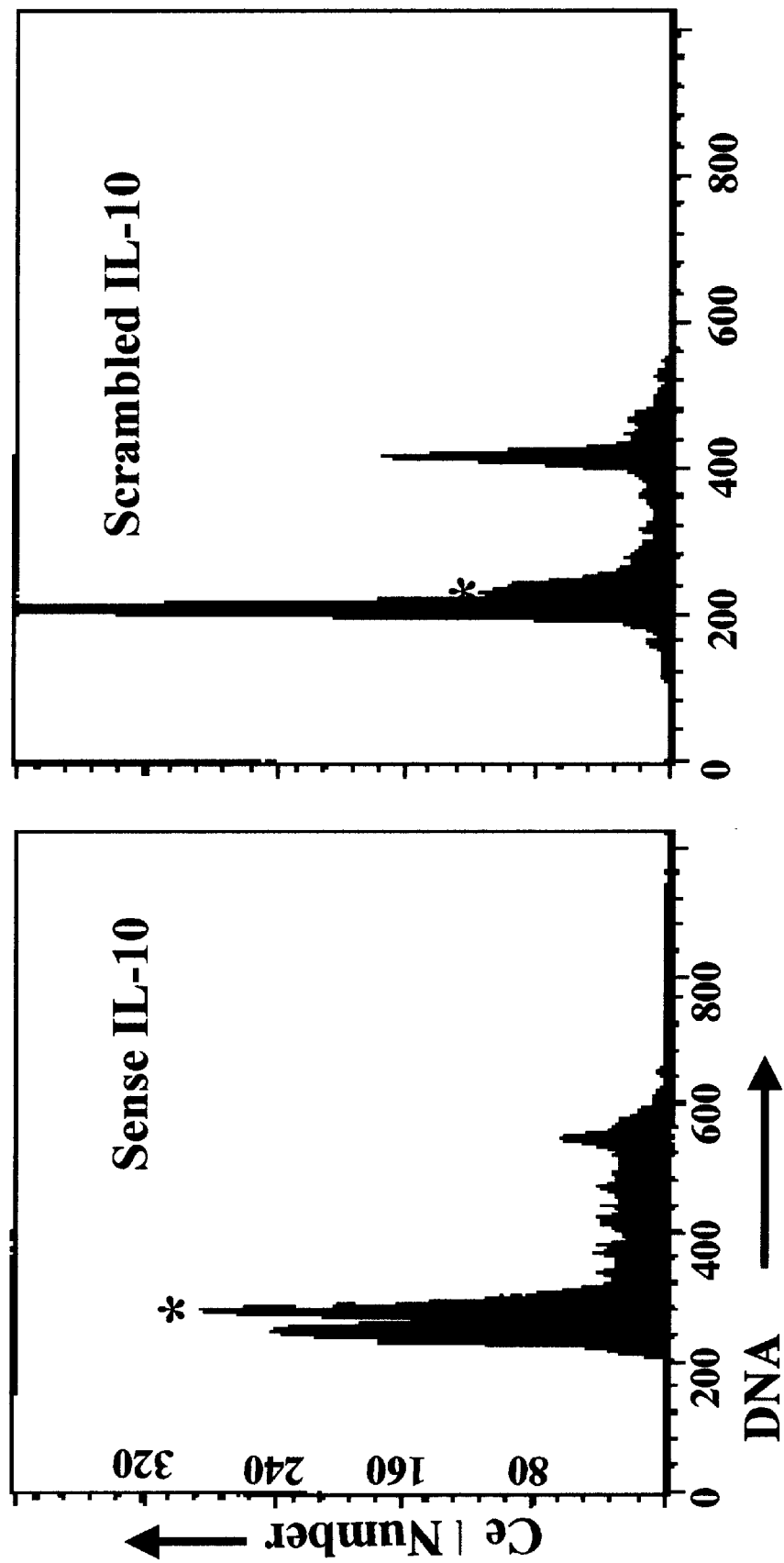
FIG. 15 is a graph showing spleens removed from recipient mice (Experiment #2, Day 40) and single cell suspensions stained with propidium iodide and analyzed by flow cytometric techniques for DNA content.
Figure 15B:
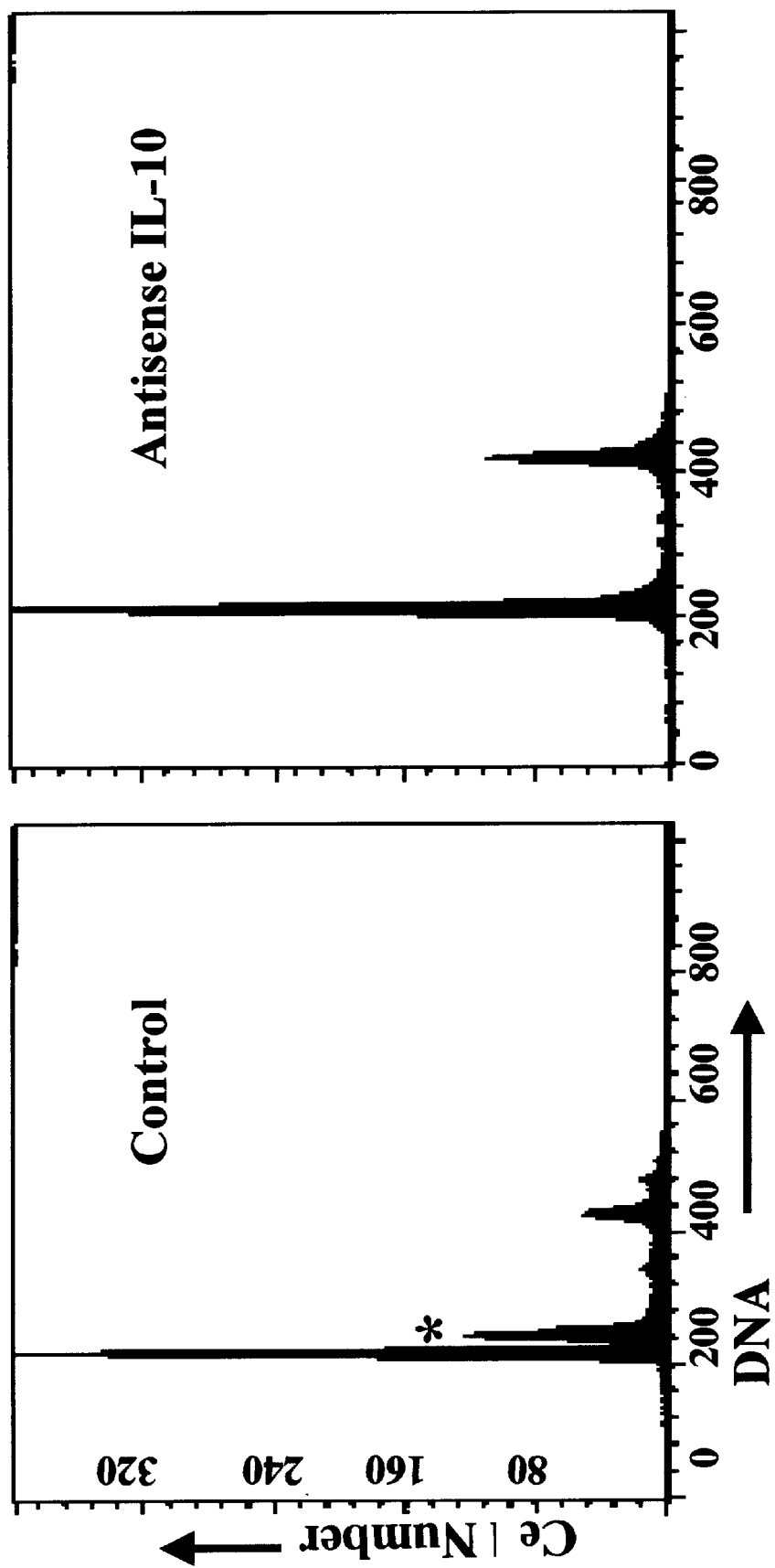
Figure 16:
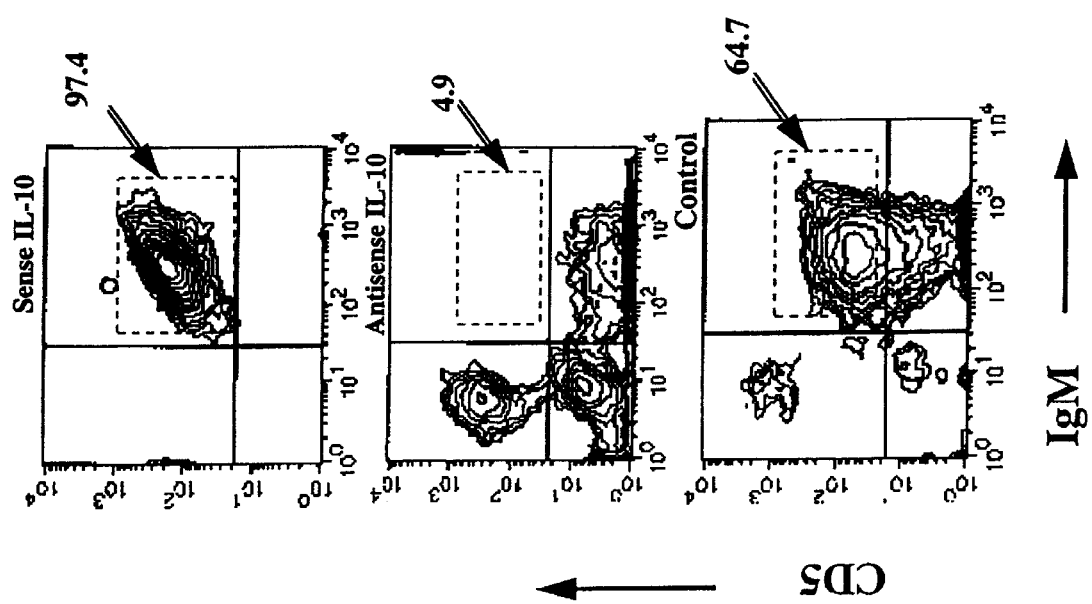
FIG. 16 is a graph showing cell surface marker expression of the spleen cells from the same anitials analyzed in FIG. 15.

In Experiment #2 only one dose of oligo (300 ug/day) was employed for the 28 days of the infusion. Mice were either sacrificed on Day 40 (a time near mean survival of untreated mice following transfer of the leukemic B-1 cells) or followed for survival. Flow cytometric analysis of DNA content on Day 40 demonstrated the presence of malignant hyperdiploid cells in various tissues of all animals not treated with antisense IL-10. Control (pump with buffer alone), scrambled antisense IL-10 and sense IL-10 all showed the typical malignant B-1 cell phenotype of hyperdiploid G1 cells which are identified by an asterisk (FIG. 15). These cells can be further identified not only on the basis of hyperdiploid DNA content, but also the presence of a clone of CD5+, IgM positive B cells (B-1) (FIG. 16). The location of the B-1 cells is highlighted by the box. The growth of the leukemic B-1 cells was prevented only in the recipients of antisense IL-10. Both the sense and control animals demonstrated a majority of the spleen cells were B-1 cells, whilethe antisense IL-10 animals had the same percental of splenic B-1 cells seen in a normal (NZB×DBA/2)F1 animal, B-1 cells represent approximately 5% of the normal splenic population.

Figure 17:
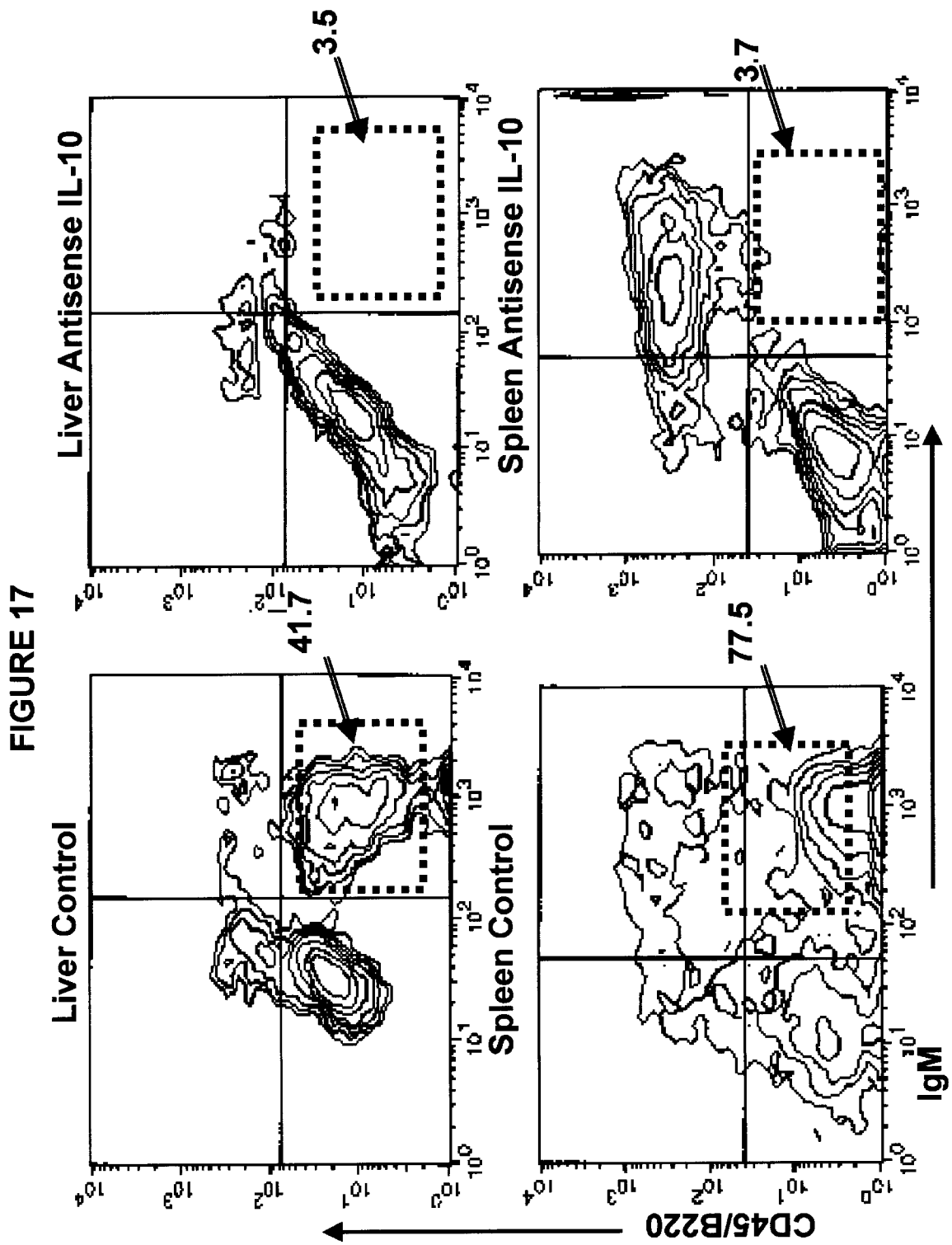
FIG. 17 is a graph showing cell surface marker expression of spleen (bottom panels) and liver (top panels) cells from animals receiving leukemic B-1 cells and treated with either buffer with pump (left) or antisense IL-10 with pump (right) for 42 Days (Experiment #2).

The malignant B-1 cells can also be identified on the basis of decreased expression of the B220 isoform of the surface signaling molecule CD45. The malignant B-1 cells have been found to be dull or negative for this isoform (95). Both liver and spleen in recipient animals which received antisense IL-10 demonstrated very few B220 dull IgM+B cells (FIG. 17). In contrast in recipient animals not receiving antisense IL-10, the liver, which normally has very few B cells, had a high percentage of malignant B-1 cells present. In addition, the spleen also contained high amounts of B220 negative B cells in recipient mice not receiving antisense IL-10.

Histopathological examination was performed on the mice treated via the mini-osmotic pumps. The recipient of antisense IL-10 had a microscopically normal liver. In contrast the liver from a recipient of sense IL-10 had diffuse sinusoidal infiltrates of neoplastic cells and small nodular neoplastic cell aggregates. Similarly the liver from a control recipient (receiving pump plus buffer, not shown) also had diffuse sinusoidal infiltrations of mononuclear neoplastic cells and prominent multifocal nodular aggregations of neoplastic cells. The spleen from antisense IL-10 treated mice appeared histologically normal. In contrast, the spleens from mice receiving sense or scrambled antisense IL-10 (figure not shown) contained sheets of large mononuclear neoplastic cells resulting in a loss of splenic architecture.

The experiments with the mini-osmotic pumps demonstrated that in vivo antisense IL-10 was effective in preventing the growth of transferred malignant B-1 cells. However, the dose was quite high (300 ug/day antisense IL-10) in order to increase survival. The total amount of oligonucleotide needed for each mouse was in the range of 8.4 mg/mouse. Thus treatment in humans would require very large amounts of antisense oligonucleotides. In addition, to prevent degradation, the oligos need to be in the form of phosphorothioates which significantly increases the cost of treatment. Thus, a simpler method of delivering the oligonucleotide was considered.

Delivery of Oligonucleotides in a Lipid Cochleate:

In these exper.iments three groups of mice were employed (4 mice/group). All (NZB×DBA/2)F1 recipients received a transfer of malignant leukemic B-1 cells. The first group was untreated. The second control group received cochleates and the third group received antisense IL-10 oligonucleotide/cochleate formulation. The oligonucleotides were not modified since the method of action of the lipid cochleates most likely is to bind directly to the membrane thus reducing the likelihood that the delivered oligonucleotides would be degraded by extracellular nucleases. The oligonucleotides were mixed with the lipids and a total of 1.3 mg of oligo/mouse was employed. The mice were injected sc with the lipid cochleate oligonucleotide as described in the Materials and Methods. The mice which received nothing or the cochleates alone were dead due to hind leg paralysis by day 3.4 (range 28–34 days). The antisense IL-10/cochleate treated group was somewhat varied in response. None of the antisense IL-10/cochleate treated group demonstrated any in vivo expansion of the leukemic B cells. However, one of the mice died on day 32 but not of hind leg paralysis. Histopathological examination of the tissue from this animal also revealed a lack of presence of neoplastic cells in the brain and spinal cord (Figure not shown). This was in contrast to mice which had received the transferred malignant cells and cochleates alone in which expansion of neoplastic cells could be observed. The soft tissue of the spinal cords had massive infiltrates of round mononuclear neoplastic cells with extensive involvement of the extradural space. Thus, the single animal in the antisense IL-10/cochleate which died early in the experiment did not die as a result of neoplastic growth that could be detected in the tissues analyzed. In addition, while all of the mice which did not receive antisense IL-10/cochleates were dead by day 34, the remaining antisense IL-10 treated group survived and were eventually killed at 6 months post transfer with no evidence of neoplastic growth and expansion determined by flow cyotmetric analysis. An additional group of seven mice not included in this analysis received the cochleates to determine if the lipid might have toxic effects. These mice lived for longer than 9 months following multiple injections of empty cochleates (these mice did not recieive any transferred malignant B-1 cells). Thus, in. the initial study of in vivo treatment of antisense IL-10/cochleate formulation to block the growth of transferred leukemic B cells, the lipid cochleates appear to be superior to constant infusion of phosphorothioate modified antisense IL-10 in preventing death due to neoplastic B-1 cell growth.

Summary of in vivo Antisense IL-10 Treatment:

In FIG. 18, a summary of the results of the effects of in vivo antisense IL-10 treatment to prevent the growth of transferred leukemic cells is presented. Both the results from experiments with mini-osmotic pumps (excluding the dosing studies) and the lipid cochleate delivery systems are combined. The results are expressed as the percentage of # diseased animals/# animals studied. Mice were considered diseased if they died of hind leg paralysis before Day 60 or had evidence of expansion of the transferred malignant B-1 cells by flow cytometric or histopathological analysis. Because these experiments required large amounts of oligo the experiments had small groups. None (0/7) of the antisense IL-10 treated mice were considered to have died of overt disease. In contrast the remaining recipients showed, in the majority of cases (18/19), the growth and metastases of the malignant leukemic B cells.

FIG. 13 is a graph showing induction of apoptosis in malignant B-1 cells in vitro. Histograms on the left represent flow cytometric analysis of cultured malignant B-1 cells. Cells were either untreated or cultured in the presence of IL-10 sense oligo or antisense IL-10 oligo. Cells were analyzed at either 24 or 48 hours following treatment. The cells were fixed and then stained with the DNA specific dye propidium iodide. The apoptotic sub-G1 cells are identified by an arrow. Panels on the right are growth inhibition as measured by a decrease in MTT between the oligo treated cultures and untreated control cultures as a function of time.

FIG. 14 is a graph showing that mice (NZB×DBA/2)F recipients which received $10 \times 10^6$ malignant B-1 cells and the mean survival in days for each group at the various concentrations is shown. At the time of transfer the mice were implanted with mini-osmotic pumps which delivered various concentrations of phosphorothioate modified oligonucleotides. The mean survival in days for each group at the various concentrations is shown. AS, antisense IL-10 treated group. SS, sense IL-10. SO, scrambled antisense. Groups contained 3 mice in each group.

FIG. 15 is a graph showing spleens from recipient mice (Experiment #2, Day 40) were removed and single cell suspensions stained with propidium iodide and analyzed by flow cytometric techniques for DNA content. Asterisk indicates the presence of hyperdiploid G1 cells. Hyperdiploidy is a characteristic of the transferred leukemic cells. Control are mice treated with the pump and buffer alone. Sense IL-10, Antisense IL-10 and Scrambled antisense IL-10 mice were treated with the phosphorothioate modified oligonucleotides in the pump as described in M&M.

FIG. 16 is a graph showing cell surface marker expression of the spleen cells from the same animals analyzed in FIG. 15. The cells were stained with anti-CD5 bio/PE and anti IgM. The transferred malignant B cells were CD5+ and IgM+ (B-1 cells). The location of these cells is indicated by the hatched box. The percent of total lymphoid cells found in that boxed area is presented on the side of each two color contour plot. Only the animal treated with antisense IL-10 did not possess a large amount of B-1 cells in the spleen.

FIG. 17 is a graph showing cell surface marker expression of spleen (bottom panels) and liver (top, panels) cells from animals receiving leukemic B-1 cells and treated with either buffer with pump (left) or antisense IL-10 with pump (right) for 42 Days (Experiment #2). The malignant B-1 cells are CD45/B220 dull/negative, IgM+ and the location of these cells on the two color contour plot is indicated by the hatched box. The percent of total lymphoid cells found in this region is indicated by the numbers on the side of each panel. The antisense IL-10 treated animal did not have large amounts of cells with this surface characteristic.

FIG. 18 is a graph summarizing in vivo antisense IL-10 experiments including both forms of delivery, pumps and cochleates. All mice were (NZB DBA/2)F1 recipients which received a transfer of leukemic B-1 cells. Percent of diseased animals in a particular treatment group is the # diseased animals/# animals studied multiplied by 100. Disease includes all mice which died before day 60 with hindleg paralysis or evidence of clones of malignant B-1 cells detected by flow cytometry or abnormal pathology at the time of sacrifice. Antisense IL-10 treated animals (0/7), sense IL-10 (4/5), control (receiving either pumps +buffer alone or cochleates alone) (7/7), untreated receiving no treatment following transfer of the leukemic B-1 cells (7/7).

Discussion

Growth Inhibition of Malignant CD5+B (B-1) Cells by Antisense Interleukin-10

Antisense therapy against cytokines may be a potential therapeutic tool for the treatment of a variety of disease states. For instance, IL-6 antisense has been employed for the treatment of renal cell carcinoma, myeloma and ovarian cancer; IL-1 antisense for the treatment of inflammatory disease and IL-11 antisense in the treatment of malignant megakaryoblastic cells (22–25, 33, 34). In this report, the effects of IL-10 antisense on malignant B-1 cells were studied.

Although IL-10 has only been identified within the last 3 years, it has been the subject of numerous investigations (8, 10, 12, 14–17, 35). Studies have suggested that IL-10 is an autocrine growth factor for B-1 cells (8, 14) and functions as a potent growth and differentiation factor for activated human B lymphocytes. In humans, B lymphomas possessed elevated levels of IL-10 which was also related to the infection by EBV (13, 19). Masood, et al (21) reported that IL-10 is an autocrine B-cell growth factor for human B cell lymphoma and their growth can be blocked by IL-10 antisense. Similarly, applicants have reported that murine malignant B-1 cells possess high levels of IL-10 mRNA (5, 6, 36). Therefore applicants speculated that the elevated IL-10 in murine malignant B-1 cells may contribute in part to their rapid growth. An IL-10 antisense treatment was designed and in vitro vulture studies performed. The results of these experiments indicated that the IL-10 antisense oligo not only inhibited the growth but also lead to cell death of malignant B-1 cell lines studied. These results showed that IL-10 is required for both the growth and survival of malignant B-1 cells studied. However, similar to the study of IL-6 antisense reported by Watson (25), the addition of exogenous rIL-10 neither stimulated the growth of these malignant B-1 cells nor reversed the inhibitory effect on these cells of IL-10 antisense oligo. One possibility is that the effe,ct of IL-10 antisense is nonspecific. This seems unlikely based on the results of several additional experiments. Two IL-10 antisense oligos targeted at different region of the IL-10 mRNA showed similar inhibitory effects, while the sense and the scrambled oligos showed no notable effects. Furthermore, the IL-10 antisense did not have any nonspecific inhibitory effects on several other cell lines. Even in the stromal cell line (LNC-F), which expressed moderate amounts of IL-10, cell growth was not inhibited by IL-10 antisense. The role of IL-10 for the stromal cell is unclear, but it does not seem to be a growth factor required for these cells. There does not appear to be a correlation between the level of IL-10 mRNA expressed and the susceptibility to growth inhibition by IL-10 antisense. A more important criterion for susceptibility to inhibition by IL-10 antisense may be the potency of IL-10 as a requisite endogenous growth factor. The fact that the addition of exogenous IL-10 did not enhance the growth of malignant B-1 cells also indicated that endogenous high levels of IL-10 seem to be required for the growth of malignant B-1 cells. Our results suggested that only endogenous IL-10 production can achieve the levels that are required for the growth of these malignant cells and the autocrine requirement could not be substituted by IL-10 replacement therapy. Since endogenous IL-10 gene activation is critical for B-1 cell expansion, inactivation of the endogenous IL-10 gene by IL-10 antisense rather than extracellular regulation of the IL-10 gene product should be more successful in controlling malignant growth.

The effect of IL-10 antisense was manifested in a time and dose dependent manner. As reported by others (37, 38), the effect of antisense increased with time. In our experiment, the inhibitory effects were maximal 72 hours after addition of the IL-10 antisense oligos to culture. Sufficient time may be required for the cells to take up the antisense oligos and for the translation of IL-10 protein to be reduced. In addition, enough time must be allowed for the cell to use up any IL-10 formed prior to the addition of antisense oligos. The results of experiments in which IL-10 antisense was removed at various time points during culture suggest the antisense need only be present in the cultures for the initial 48 hours to reach near peak inhibition observed it 72 hours. Not only is there a time dependence for antisense IL-10 growth inhibition, there is also a dose dependence of antisense. As shown in FIG. 4, sufficient amount of IL-10 antisense is also required for growth inhibition effect (>5 $\mu$M). This may be due to the rapid degradation and the low efficiency of cellular uptake of the unmodified oligos employed. Phosphorothioate modified antisense oligos which are more resistant to degradation and in vivo experiments are being conducted in our laboratory. Applicants have reported that malignant B-1 cells of NZB mice undergo apoptosis induced by anti-IgM antibodies (39). Applicants observed that the P12-L malignant B-1 cells also undergo apoptosis after being treated with IL-10 antisense oligos for 48 hours. This may indicate that both a strong stirmulation via cross linking the antigen receptor or a lack of growth factor will leacd the malignant cells to die by a programmed form (apoptosis).

Evidence suggests that a cytokine network regulates the production of various cytokines. The production of IFN-gamma is inhibited by IL-10 (32). It has been reported that human chronic lymphocytic leukemia cells which are very slow growing express detectable IFN-gamma mRNA and IFN-gamma can induce proliferation and differentiation in B-chronic lymphocytic leukemia cells (31, 40). However, this is not the case in our experiment system. The aggressive murine malignant B-1 cells studied herein do not possess detectable IFN-gamma mRNA as assayed by PCR (6). Our re-cent experiments have also shown that the IL-10 antisense treatment does not leLd to the production of IFN-gamma at any time point studied (up to 72 hours) as detected by ELISA. In addition, culture supernatants from the IL-10 antisense treated cells do not accelerate or block the growth of the untreated cells (data not shown). IFN-gamma has also been shown to be an inhibitory factor for the growth of CD5 +B cells (41). There is a possibility that if IL-10 prevents the production of IFN-gamma by the malignant B-1 cells, the decreased growth of the malignant B-1 cells following the IL-10 antisense treatment is due to the increased IFN-gamma production which may then exert the inhibitory effect. However, no detectable IFN-gamma mRNA and protein may exclude the possibility that the growth inhibition observed by the IL-10 antisense treatment is due to the IFN-gamma production.

Several viruses have genes with homology to IL-10 (27, 42). The EBV has a gene BCRFI with homology to the human IL-10 gene and infection with this virus results in the immortalization of B cells and the overexpression of B-cell derived endogenous IL-10 (13, 19). The increased production of IL-10 may be responsible for the growth and/or development of some human B cell malignancies. Antisense IL-10 treatment may have a role in reducing viral effects and abnormal B cell proliferation.

In summary our results showed that IL-10 may be an autocrine growth factor for malignant B-1 cells and that antisense therapy directed at IL-10 may be a potential tool in modulation of B cell leukemias.

Antisense Interleukin-10 Effects on Chronic Lymphocytic Leukemia Cell Growth

In this report, applicants found that a subpopulation of all B-chronic lymphocytic leukemia patients respond to antisense-IL-10 by demonstrating a significant decrease of cell growth in culture. These responding chronic lymphocytic leukemia patients are similar to the NZB mouse model in which all the B-1 malignant cells produce hi,gh levels of IL-10. In this murine model, applicants have found that in addition to an in vitro inhibitory effect of antisense IL-10, in vivo prolonged antisense IL-10 administration also prevented malignant B-1 cell growth (51). Antisense therapy against cytokines may be a potential therapeutic tool for the treatment of a variety of disease states. For instance, IL-6 antisense has been employed for the treatment of renal cell carcinoma, myeloma and ovarian cancer; IL-1 antisense for the treatment of inflammatory disease and IL-11 antisense in the treatment of malignant megakaryoblastic cells (62–65, 71, 72) In addition to cytokine antisense therapy, bcl-2 has also been targeted for antisense therapy (73)

In this report aLnd previous reports (53, 74), the levels of IL-10 mRNA in malignant B-1 cells were found to be varied. Previous investigators have reported a variety of cytokines to be elevated in B-chronic lymphocytic leukemia (75–78). Cytokines not only promote the growth of B-1 malignant cells but can also regulate their growth (43, 75). Other investigators (70) have found that exogenous IL-10 was inhibitory for B-chronic lymphocytic leukemia cell, however, under the experimental conditions employed in this report applicants were unable to find any apoptotic effects of IL-10 over a wide concentration range (10–100 ng/ml) tested. In the current study, IL-10 mRNA was found to be elevated in only some chronic lymphocytic leukemia patients. It is not surprising that there was a correlation between growth inhibition by antisense IL-10 in the B-chronic lymphocytic leukemia patients and the level of IL-10 message. It appears that only in the situation in which IL-10 is an autocrine growth factor can growth inhibition by IL-10 antisense be effective.

In our analysis of the murine model of chronic lymphocytic leukemia, applicants have found that IL-10 plays a central role in the development of B-chronic lymphocytic leukemia like malignancies. Previous studies in mice have shown that IL-10 is not required for the development of B-1 cells (79). However in NZB mice, B-1 malignant growth does seem to be dependent upon IL-10 levels. In the current study, applicants found that increased CD5+B cells in the peripheral blood, which is a hallmark of chronic lymphocytic leukemia, was partially correlated to the levels of IL-10. Perhaps, other cytokines in addition to IL-10 can provide growth signals for B-1 cells. Cytokines may not solely be responsible for malignant B-1 development and growth, other genetic alteration involving oncogenes, such as bcl-2, may be required for malignant B-1 cell development.

Although IL-10 has only been identified within the last 3 years, it has been the subject of numerous investigations (54). Studies have suggested that IL-10 is an autocrine growth factor for B-1 cells (54, 59) and functions as a potent growth and differentiation factor for activated human B lymphocytes. In humans, B lymphomas possessed elevated levels of IL-10 which was also related to infection by EBV (56, 80). Masood, et al. (61) reported that IL-10 is an autocrine B-cell growth factor for human B cell lymphoma and their growth can be blocked by IL-10 antisense. Similarly, applicants have reported that murine malignant B-1 cells possess high levels of IL-10 mRNA and are susceptible to antisense IL-10 inhibition (51, 52, 81). In the present report, applicants found that IL-10 antisense not only inhibits the growth but and also lead to cell death of malignant B-1 cells in some patients with chronic lympho-clitic leukemia.

The effect of IL-10 antisense was manifested in a time and dose dependent manner. As reported by others (82, 83), the effect of antisense increased with time. In our experiment, the inhibitory effects were maximal at a concentration of 20 $\mu$m, at 72 hours after addition of the IL-10 antisense oligos to culture. Sufficient time may be required for the cells to take up the antisense oligos and for the translation of IL-10 protein to be reduced. In addition, enough time must be allowed for the cell to deplete residual IL-10 protein formed prior to the addition of antisense oligos.

In summary ouir results showed that IL-10 may be an autocrine growth factor for malignant B-1 cells and that antisense therapy directed at IL-10 may be a potential tool in modulation of some B cell leukemias.

Throughout this application, various publications have been referenced. The disclosures in these publications are incorporated herein by reference in order to more fully describe the state of the art.

In Vivo Antisense IL-10 Prevents Expansion of a B-1 Leukemia/Lymphoma

In these experiments, in vivo treatment with antisense IL-10 was able to inhibit the growth of a transferred B-1 malignant lymphoma. Antisense therapy against cytokines may be a potential therapeutic tool for the treatment of a variety of disease states. In vivo use of antisense therapy has been shown to be effective in experimental models of malignancy (96–36) and doses of up to 100 mg/kg per day in rodents have been found to be well tolerated (99). The antisense has been delivered in vivo by a variety of methods including phosphorothioate modified oligos to protect against nuclease degradation in vivo (104, 99), as well as lipid based matrix delivery systems (105, 106) and constant infusion pumps (107) (108). Currently the use of antisense for the treatment of patients is in the clinical trial phase. For example, a clinical trial to investigate the efficacy of in vivo antisense c-fos in metastatic breast cancer (Protocol VU BRE-29, NCI V95-0649) and the use of ex vivo purged bone marrow cells treated with antisense c-myb for the treatment of chronic myelogenous leukemia (Protocol UPCC 3492, NCI V94-0532) are currently underway. In addition, antisense ICAM-1 is currently in Phase II clinical trials with the oligonucleotikle delivered intravenously over 26 days with 13 infusions. In this report, the in vivo effects of IL-10 antisense on malignant B-1 cells was studied using several different delivery systems and doses. Although these results are preliminary, all of the methods of delivering antisense IL-10 prevented or delayed the growth of the malignant B-1 cells.

Although IL-10 has only been identified within the last 5 years, it has been the subject of numerous investigations. Studies have suggested that IL-10 is an autocrine growth factor for B-1 cells (10, 14) and functions as a potent growth and differentiation factor for activated human B lymphocytes. In humans, B lymphomas possessed elevated levels of IL-10 which was also related to the infection by EBV(13, 19). It has been reported that IL-10 is an autocrine B-cell growth factor for human B cell lymphomas and their growth can be blocked by IL-10 antisense in vitro (87, 91), antibodies against IL-10 or soluble IL-10R (109). Similarly, it has been reported that murine malignant B-1 cells possess high levels of IL-10 mRNA (8). Therefore it was speculated that the elevated IL-10 in murine malignant B-1 cells may contribute in part to their rapid growth. IL-10 antisense treatment in vitro not only inhibited the growth but also lead to cell death of malignant B-1 cell lines studied and this effect was specific since sense and scrambled antisense did not show these effects (91). In addition., antisense IL-10 had no inhibitory effect on normal B cells or other cell lines in which IL-10 was not an autocrine growth factor. These results suggested that endogerious IL-10 gene activation is critical for B-1 cell expansion and that inactivation of the endogenous IL-10 gene by IL-10 antisense rather than extracellular regulation of the IL-10 gene product should be more successful in controlling malignant growth.

We have previously performed extensive genetic analysis of the inheritance of autoimmune traits in NZB mice and their hybrids (91, 110–114). These studies indicated that the autoimmune disease in NZB mice was dependent upon the action of several genes, some of which were linked. At twelve months of age nearly all NZB mice have a clonal expansion of B-1 cells in the spleen and peritoneum. These are identified as $CD5^+$, $B220^{dull}$, $IgM^+$ and hyperdiploid. Recent work in NZB backcrosses has indicated that high levels of IL-10 are strongly linked to the presence of lymphoproliferative disease of B-1 cells (8). In summary, the results showed that IL-10 may be an autocrine growth factor for malignant B-1 cells and that antisense therapy directed at IL-10 may be a potential tool in modulation of B cell leukemias.

Evidence suggests that a cytokine network regulates the production of various cytokines. The production of IFN-g is inhibited by IL-10 (115). It has been reported that human CLL cells which are very slow growing express detectable IFN-g mRNA and IFN-g can induce proliferation and differentiation in B-CLL cells (116). Despite the possible effect of IFN-g upregulation by antisense IL-10 in vivo, the overall effect of antisense IL-10 was to block the growth of the murine CLL cells.

The in vivo effect of IL-10 antisense was manifested in a dose dependent manner. Lower doses of antisense IL-10 (less than 30 ug/day) when delivered in the mini-osmotic pump under constant infusion for 28 days were much less effective in preventing the growth of transferred malignant B-1 cells. In order to prevent the growth of malignant B-1 cells in vivo, 300 ug/day must be constantly infused for 28 days resulting in a total of 8.4 mg phosphorothioate modified antisense IL-10 oligonucleotide. In contrast, much lower doses of antisense IL-10 were effective in preventing the growth of malignant B-1 cells when the oligonucleotides were delivered in a formulation in which the bulk of the unmodified oligonucleotides were delivered encapsulated in a lipid formulation in the presence of high calcium concentrations. The reasons for this increased efficacy of antisense IL-10 when encapsulated in the cochleates might be due to increased ability of the lipid based cochileates to attach to the cell membrane and deliver the oligonucleotides to the cell and preventing possible nuclease degradation. In addition, due to the rolled nature of the cochleates and their gradual unwinding in the presence of lower calcium concentration in vivo, the antisense IL-10 may be released slowly over a prolonged period of time. Thus the four injections of antisense IL-10/cochleates (1.3 mg total) allowed for sustained antisense IL-10 activity intercellularly.

Many possible uses of antisense IL-10 are possible in the prevention of the growth of malignant B-1 cells similar to that seen in human CLL. In the present experiments, the recipient animals were given an injection of malignant cells which rapidly grew in the recipient animals. The growth of these transferred cells could easily be monitored by DNA content, cell surface markers and abnormal pathology. The mice died with a characteristic hindleg paralysis due to the growth of these cells in regions surrounding the spinal column. The question still remains if antisense IL-10 will be effective in preventing the further growth of an endogenous leukemia or lymphoma. We have sought to determine the role of IL-10 in endogenous malignancies in NZB mice by generating NZB IL-10 knockout mice. In the future we plan to administer IL-10 to NZB mice before and after the development of B-1 malignancies. The results from the current experiments suggest the dose and method of delivery of the antisense IL-10 which will optimize the regulatory effects on the growth of the B-1 malignancy.

REFERENCES

1. Kantor A. (1991) A new nomenclature for B cells. Immunol Today. 12, 388.

2. Foon K. A., Rai K. & Gale R. (1990) CLL: new insights into biology and therapy. Ann. Intern. Med. 113, 525.

3. Phillips J., Mehta K., Fernandez C. & Raveche E. (1992) The NZB mouse as a model for CLL. Cancer Res. 52, 437.

4. Okamoto H., Nishimura H., Shinozaki A., Zhang D., Hirose S. & Shirai T. (1993) H-2z hoinozygous New Zealand mice as a model for B-cell chronic lymphocytic leukemia.: elevated bcl-2 expression in CD5 B cells at premalignant and malignant stages. Jpn. J. Cancer Res. 84, 1273.

5. Lin T., Svetic A., Ganea D., Rameshwar P., Gascon P., Gause W. & Raveche E. (1992) Cytokines in CD5+B cells. Ann NY Acad Sci. 651, 581.

6. Peng B., Sherr D. H., Mahboudi F., Hardin J., Sharer L. & Raveche E. S. (1994) A cultured malignant B-1 line serves as a model for Richter's syndrome. J. Immunol. 153, 1869.

7. Finke J., Ternes P., Lange W., Mertelsmann R. & Dolken G. (1993) Expression of Interleukin 10 in B lymphocytes of different origin. Leukemia. 7, 1852.

8. Moore K. W., O'Garra A., de Waal Malefyt R., Vieira P. & Mosmann T. R. (1993) IL-10. Ann. Rev. Immunol. 11, 165.

9. Fiorentino D. F., Bond M. W. & Mosmann T. R. (1989) Two types of mouse helper T cell. IV. Th2 clones secrete a factor that inhibits cytokine production by Th1 clones. J. EXP. Med. 170, 2081.

10. MacNeil I., Suda T., Moore K., Mosmann T. & Zlotnik A. (1990) IL-10, A novel growth cofactor for mature and immature T cells. J. Immunol. 145, 4167.

11. Thompson-Snipes L., Dhar V., Bond M. W., Mosmann T. R., Moore K. W. & Rennick D. (1991) Interleukin-10: a novel stimulatory factor for mast cells and their progenitors. J. Exp. Med. 173, 507.

12. O'Garra A., Chang R., Go N., Hastings R., Haughton G. & Howard M. (1992) Ly-1 B (B-1) cells are the main source of B cell-derived interleukin 10. Eur. J. Immunol. 22, 711.

13. Burdin N., Peronne C., Banchereau J. & Rousset F. (1993) Epstein-Barr virus transformation induces B lymphocytes to produce human interleukin 10. J Exp Med. 177, 295.

14. de Waal Malefyt R., Abrams J., Bennett B., Figdor C. & deVries J. (1991) IL-10 inhibits cytokine synthesis by human monocytes: an autoregulatory role of IL-10 produced by monocytes. J. Exp. Med. 174, 1209.

15. Rousset F., Garcia E., Defrance T., Peronne C., Vezzio N., Hsu D. H., Kastelein R., Moore K. W. & Banchereau J. (1992) Interleukin 10 is a potent growth and differentiation factor for activated human B lymphocytes. Proc. Natl. Acad. Sci. USA. 89, 1890.

16. O'Garra A., Stapleton G., Dhar V., Pearce M., Schumacher J., Rugo D., Barbis D., Stall A., Cupp J., Moore K., Vieira P., Mosmann T., Whitmore A., Arnold L., Haughton G. & Howard H. (1990) Production of cytokines by mouse B cells: B lymphomas and normal B cells produce IL-10. Int. Immunol. 2, 821.

17. Vieira P., de Waal-Malefyt R., Dang M. N., Johnson K. E., Kastelein R., Fiorentino D. F., deVries J. E., Roncarolo M. G., Mosmann T. F. & Moore K. W. (1991) Isolation and expression human cytokine synthesis inhibitory factor (CSIF/IL-10) cDNA clones: homology to EBV open reading frame BCRF1. PNAS. 88, 1172.

18. Hsu D. H., de Waal Malefyt R., Fiorentino D., Dang M. N., Vieira P., deVries J., Spits H., Mosmann T. & Moore K. (1990) Expression of interleukin-10 activity by Epstein-Barr virus protein BCRF1. Science. 250, 830.

19. Benjamin D., Knobloch T. J. & Dayton M. A. (1992) Human B-cell interleukin-10: B-cell lines derived from patients with acquired immunodeficiency syndrome and Burkitt's lymphoma constitutively secrete large quantities of interleukin-10. Blood. 80, 1289.

20. Miyazaki I., Cheung R. K. & Dosch H. M. (1993) Viral interleukin 10 is critical for the induction of B cell growth transformation by Epstein-Barr virus. J. Exp. Med. 178, 439.

21. Masood R., Bond M., Scadden D., Kaplan M., Levine A. M. & Gill P. S. (1992) Interleukin-10: an autocrine B-cell growth factor for human B-cell lymphoma and their progenitors. Blood. 80, 115.

22. Levy Y., Tsapis A. & Brouet J. C. (1991) Interleukin-6 antisense oligonucleotides inhibit the growth of human myeloma cell lines. J. Clin. Invest. 88, 696.

23. Barut B., Chauhan D., Uchiyama H. & Anderson K. C. (1993) Interleukin-6 functions as an initracellular growth factor in hairy cell leukemia in vitro. J. Clin. Invest. 92, 2346.

24. Fujita J., Takenawa J., Kaneko Y., Okumura K. & Yoshida O. (1992) Anti-interleukin-6 (IL-6) therapy of IL-6-producing renal cell carcinoma. Hinyokika Kiyo-Acta Urologica Japonica. 38, 1333.

25. Watson J. M., Berek J. S. & Martinez-Maza O. (1993) Growth inhibition of ovarian cancer cells induced by antisense IL-6 oligonucleotides. Gynecol. Oncol. 49, 8.

26. Chen W. & Zlotnik A. (1991) IL-10: A novel cytotoxic T cell differentiation factor. J. Immunol. 147, 528.

27. Moore K., Vieira P., Fiorentino D., Trounstine M., Khan T. & Mosmann T. (1990) Homology of cytokine synthesis inhibitory factor (IL-10) to the Epstein-Barr Virus Gene BCRF1. Science. 248, 1230.

28. Svetic A., Finkelman F. D., Jian Y. C., Dieffenbach C. W., Scott D. E., Mccarthy K. F., Steinberg A. D. & Gause W. C. (1991) Cytokine Gene Expression After Invivo Primary Immuunization with Goat Antibody to Mouse IgD Antibody. J. Immunol. 1417, 2391.

29. Mosmann T. (1983) Rapid calorimetric Assay for cellular growth and survival: application to proliferation and cytotoxicity assays. J. Immunol. Methods. 65, 55.

30. Denizot F. & Lang R. (1986) Rapid colorimetric assay for cell growth and survival modifications to the tetrazolium dye procedure giving improved sensitivity and reliability. J Immunol Methods. 89, 271.

31. Buschle M., Campana D., Carding S., Richard C., Hoffbrand A. V. & Brenner M. K. (1993) Interferon-ganmna inhibits apoptotic cell death in B-CLL. J.Exp.Med. 177, 213.

32. Chomarat P., Rissoan M.-C., Banchereau J. & Miossec P. (1993) Interferon g inhibits int-rleukin 10 production by monocytes. J. Exp. Med. 177, 523.

33. Burch R. M. & Mahan L. C. (1991) Oligonucleotides antisense to the interleukin 1 receptor mRNA block the effects of interleukin 1 in cultured murine and human fribroblasts and in mice. J. Clin. Invest. 88, 1190.

34. Kobayashi S., Teramura M., Sugawara I., Oshimi K. & Mizoguchi H. (1993) Interleukin-11 acts as an autocrine growth factor for human megakaryoblastic cell lines. Blood. 81, 889.

35. Tan J. C., Indelicato S. R., Narula S. K., Zavodnk P. J. & Chou C. C. (1993) Characterization of Interleukin-10 Receptors on Human and Mouse Cells. J. Biol. Chem. 268, 21053.

36. Lin T., Fernandes H., Yauch R., Ponzio N. & Raveche E. (1992) IL-10 production in a CD5+B cell lymphoma arising in a anti-CD4 monoclonal antibody treated SJL. Clin. Immunol. Immunopathol. 65, 10.

37. Reed J. C., Stein C. A., Subasinghe C., Haldar S., Croce C., Yum S. & Cohen J. (1990) ikntisense-mediated inhibition of BCL2 protooncogene expression and leukemic cell growth and survival: Comparisons of phosphodiester and phosphorothioate oligodecxynucleotides. Cancer Res. 50, 6565.

38. Morrison R. S. (1991) Suppression of basic fibroblast growth factor expression by antisense oligodeoxynucleotides inhibits the growth of transformed human astrocytes. J. Biol. Chem. 266, 728.

39. Peng B. & Raveche E. (1993) Apoptosis Induction of B-1 Malignant clones from a murine model of CLL. Leukemia. 7, 789.

40. Ostlund L., Einhorn S. & Robert K. H. (1986) Chronic B-lymphocytic leukaemia cells proliferate and differentiate upon exposure to interferon in vitro. Blood. 67, 152.

41. Ishida H., Hastings R., Kearney J. & Howard M. (1992) Continuous anti-interleukin 10 antibody administration depletes mice of Ly-1 cells but not conventional B cells. J. Med. Exp. 175, 1213.

42. Rode H. J., Janssen W., Rosen-Wolff A., Bugert J. J., Thein P., Becker Y. & Darai G. (1993) The genome of equine herpesvirus type 2 harbors an interleukin 10 (IL10)-like gene. Virus Genes. 7, 111.

43. Caligaris-Cappio F., Gottardi D., Alfarano A., Stacchini A., Gregoretti M., Ghia P., Bertero M., Novarino A. and Bergui L.: The nature of the B lymphocyte in B-CLL. Blood Cells. 601–613, 1993.

44. Korsmeyer S. J.: Bcl-2: a repressor of lymphocyte death. Imm. Today. 13, 285–287, 1992.

45. Caligaris-Cappio F., Ghis P., Gottardi D., Parvis G., Gregoretti M., Nilsson K. and Schena M.: The role of bcl-2 in the natural history of B-CLL. Curr.Topics Micro. Immunol. 182, 279–286, 1992.

46. Kantor A.: A new nomenclature for B cells. Immunology Today. 12, 388, 1991.

47. Stall A., Farinas M., Tarlinton D., Lalor P., Herzenberg L., Strober S. and Herzenberg L.: Ly-1 B cell clones similar to human CLL routinely develop in older normal mice and young autoimmune NZB related animals. PNAS. 85, 7312–7316, 1988.

48. Shirai T., Okada T. and Hirose S.: Genetic regulation of CD5+B cells in autoimmune disease and in CLL. Ann NY Acad. Sci. 651, 509–526, 1992

49. Phillips J., Mehta K., Fernandez C. and Raveche E.: The NZB mouse as a model for CLL. Cancer Res. 52, 437–443, 1992.

50. Peng B., Sherr D. H., Mahboudi F., Hardin J., Sharer L. and Raveche E. S.: A cultured malignant B-1 line serves as a model for Richter's syndrome. J. Immunol. 19, 159–167, 1995.

51. Peng B., MUehta N., Fernandes H., Chou C. and Raveche E.: Growth inhibition of maligrnant CD5+B (B-1) cells by antisense IL-10 oligonucleotide. Leu. Res. 19, 159–167, 1995.

52. Lin T., Fernandes H., Yauch R., Ponzio N. and Raveche E.: IL-10 production in a CD5+B; cell lymphoma arising in a anti-CD4 monoclonal antibody treated SJL. Clin. Immunol. Immunopathol. 65, 10–22, 1992.

53. Finke J., Ternes P., Lange W., Mertelsmann R. and Dolken G.: Expression of IL-10 in B lymphocytes of different origin. Leukemia. 7, 1852–1857, 1993.

54. Moore K. W., O'Garra A., de Waal Malefyt R., Vieira P. and Mosmann T. R.: IL-10. Ann. Rev. Immunol. 11, 165–190, 1993.

55. O'Garra A. and Howard M.: IL-10 Production by CD5 B Cells. Ann. NY. Acad. Sci. 651, 182–199, 1992.

56. Burdin N., Peronne C., Banchereau J. and Rousset F.: Epstein-Barr virus transformation induces B lymphocytes to produce human interleukin 10. J Exp Med. 177, 295–304, 1993.

57. Moore K., Vieira P., Fiorentino D., Trounstine M., Khan T. and Mosmann T.: Homology of cytokine synthesis inhibitory factor (IL-10) to the Epstein-Barr Virus Gene BCRF1. Science. 248, 1230–1234, 1990.

58. Miyazaki I., Cheung R. K. and Dosch H. M.: Viral interleukin 10 is critical for the induction of B cell growth transformation by Epstein-Barr virus. J. Exp. Med. 178, 439–447, 1993.

59. de Waal Malefyt R., Abrams J., Bennett B., Figdor C.and deVries J.: IL-10 inhibits cytokine synthesis by human monocytes: an autoregulatory role of IL-10 produced by monocytes. J. Exp. Med. 174, 1209–1220, 1991.

60. Rousset F., Garcia E., Defrance T., Peronne C., Vezzio N., Hsu D. H., Kastelein R., Moore K. W. and Banchereau J.: Interleukin 10 is a potent growth and differentiation factor for activated human B lymphocytes. Proc. Natl. Acad. Sci. USA. 89, 1890–1893, 1992.

61. Masood R., Bond M., Scadden D., Kaplan M., Levine A. M. and Gill P. S.: Interleukin-10: an autocrine B-cell growth factor for human B-cell cell lymphoma and their progeritors. Blood. 80, 115a, 1992.

62. Levy Y., Tsapis A. and Brouet J. C.: Interleukin-6 antisense oligonucleotides inhibit the grcwth of human myeloma cell lines. J. Clin. Invest. 88, 696–699, 1991.

63. Barut B., Chauhan D., Uchiyama H. and Anderson K. C.: Interleukin-6 functions as an intracellular growth factor in hairy cell leukemia in vitro. J. Clin. Invest. 92, 2346–2352, 1993.

64. Fujita J., Takenawa J., Kaneko Y., Okumura K. and Yoshida O.: Anti-interleukin-6 (IL-6) therapy of IL-6-producing renal cell carcinoma. Hinyokika Kiyo-Acta Urologica Japonica. 38, 1333–1336, 1992.

65. Watson J. M., Berek J. S. and Martinez-Maza O.: Growth inhibition of ovarian cancer cells induced by antisense IL-6 oligonucleotides. Gynecol. Oncol. 49, 8–15, 1993.

66. Denizot F. and Lang R.: Rapid colorimetric assay for cell growth and survival modifications to the tetrazolium dye procedure giving improved sensitivity and reliability. J Immunol Methods. 89, 271–277, 1986.

67. Vieira P., de Waal-Malefyt R., Dang M., Johnson K. E., de Vries J. E., Roncarolo M., Mosmann T. R. and Moore K. W.: Isolation and expression of IL-10 cDNA clones: homology to Epstein-Barr virus open reading frame BCRF1. PNAS. 88, 1172–76, 1991.

68. McConkey D., Aguilar-Santelises M., Hartzell P., Eriksson I., Mellstedt H., Orrenius S. and Jondal M.: Induction of DNA fragmentation in Chronic B Lymphocytic Leukemia Cells. J. Immunol. 146, 1072–1076, 1991.

69. Peng B. and Raveche E.: Apoptosis Induction of B-1 Malignant clones from a murine model of CLL. Leukemia. 7, 789–794, 1993.

70. Fluckigei A., Durand I. and Banchereau J.: IL-10 induces apoptotic cell death of B-CLL. J. Exp. Med. 179, 91–99, 1994.

71. Burch R. M. and Mahan L. C.: Oligonucleotides antisense to the interleukin 1 receptor mRNA block the effects of interleukin 1 in cultured murine and human fribroblasts ind in mice. J. Clin. Invest. 88, 1190–1196, 1991.

72. Kobayashi S., Teramura M., Sugawara I., Oshimi K. and Mizoguchi H.: Interleukin-11 acts as an autocrine growth factor for human megakaryoblastic cell lines. Blood. 81, 889–893, 1993.

73. Reed J. C., Stein C., Subasinghe C., Haldar S., Croce C. M., Yum S. and Cohen J.: Antisense-mediated inhibition of bcl-2 protoncogene expression and leukemic cell growth and survival. Canc. Res. 56, 6565–6570, 1990.

74. Plate J. M. D., Knospe W. H., Harris J. E. and Gregory S. A.: Normal and aberrant expression of cytokines in neoplastic cells from CLL. Human Imm. 36, 249–258, 1993.

75. Nilsson K. The control of Growth and Differentiation in B-CLL. London: M. Dekker, 1992:33. (Cheson BD, ed. Chronic Lymphocytic Leukemia: Scientific Advances and Clinical Developments 76. di Celle P. F., Carbone A., Marchis D., Zhou D., S. S., Zupo S., Pini M., A. M. and Foa R.: Cytokine gene expression in B-CLL: Evidence of constitutive IL-8 mRNA expression and secretion of biologicallly active IL-8 protein. Blood. 84, 220–228, 1994.

77. Kooten E. V., Rensink I., Aarden L. and Van Oers R.: Cytokines and intracellular signals involved in the regulation of B-CLL proliferation. Leu and Lymph. 12, 27–33, 1993.

78. Long B. W., Witte P. L., Abraham G. N., Gregroy S. A. and Plate J. M. D.: Apoptosis and IL-7 gene expression in B-CLL. PNAS. 92, 1416–1420, 1995.

79. Kuhn R., Lohler J., Rennick D., Rajewsky K. and Muller W.: IL-10 deficient mice develop chronic enterocolitis. Cell. 75, 263–274, 1993.

80. Benjamin D., Knobloch T. J. and Dayton M. A.: Human B-cell interleukin-10: B-cell lines derived from patients with acquired immunodeficiency syndrome and Burkitt's lymphoma constitutively secrete large quantities of interleukin-10. Blood. 80, 1289–1298, 1992.

81. Lin T., Svetic A., Ganea D., Rameshwar P., Gascon P., Gause W. and Raveche E.: Cytokines in CD5+B cells. Ann NY Acad Sci. 651, 581–583, 1992.

82. Reed J. C. Stein C. A., Subasinghe C., Haldar S., Croce C., Yum S. and Cohen J.: Antisense-mediated inhibition of BCL2 protooncogene expression and leukemic cell growth and survival: Comparisons of phosphodiester and phosphorothioate oligodeo,(ynucleotides. Cancer Res. 50, 6565–6570, 1990.

83. Morrison R. S.: Suppression of basic fibroblast growth factor expression by antisense oligodeoxynucleotides inhibits the growth of transformed human astrocytes. J. Biol. Chem. 266, 728–734, 1991.

84. Ramachandra, S., R. Metcalf, T. Fredrickson, G. Marti, and E. Raveche. 1996. Requirement for increased IL-10 in the development of B-1 lymphoproliferative disease in a murine model of CLL. J CLin Invest. 98: 1788–1793.

85. Benjamin, D., T. J. Knobloch, and M. A. Dayton. 1992. Human B-cell interleukin-10: B-cell lines derived from patients with acquired immunodeficiency syndrome and Burkitt's lymphoma constitutively secrete large quantities of interleukin-10. Blood. 80: 1289–1298.

86. Miyazaki, I., R. K. Cheung, and H. M. Dosch. 1993. Viral interleukin 10 is critical for the induction of B cell growth transformation by Epstein-Barr virus. J. Exp. Med. 178: 439–447.

87. Masood, R., Y. Zhang, M. Bond, D. T. Scadden, T. Moudgil, R. Law, M. Kaplan, B. Jung, B. Espina, Y. Lunardi-Iskandar, A. Levine, and P. Gill. 1995. IL-10 is an autocrine growth factor for acquired immunodeficiency syndrome-related B cell Lymphoma. Blood. 85: 3423–3430.

88. Burch, R. M., and L. C. Mahan. 1991. Oligonucleotides antisense to the interleukin 1 receptor mRNA block the effects of interleukin 1 in cultured murine and human fribroblasts ind in mice. J. Clin. Invest. 88: 1190–1196.

89. Kobayashi, S., M. Teramura, I. Sugawara, K. Oshimi, and H. Mizoguchi. 1993. Interleukin-11 acts as an autocrine growth factor for human megakaryoblastic cell lines. Blood. 81: 889–893.

90. Moore, K., P. Vieira, D. Fiorentino, M. Trounstine, T. Khan, and T. Mosmann. 1990. Homology of cytokine synthesis inhibitory factor (IL-10) to the Epstein-Barr Virus Gene BCRF1. Science. 248: 1230–1234.

91. Peng, B., N. Mehta, H. Fernandes, C. Chou, and E. Raveche. 1995. Growth inhibition of malignant CD5+B (B-1) cells by antisense IL-10 oligonucleotide. Leu. Res. 19: 159–167.

92. Nicoletti, I., G. Migliorati, M. Pagliacci, F. Grignani, and C. Riccardi. 1991. A rapid simple method for measuring thymocyte apoptosis by propidium iodide staining andi flow cytometry. J. of Immunol. Meth. 139: 271–279.

93. Gould-Fogerite, S., and R. Mannino. "Targeted fusogenic liposomes." Liposome Technology. Ed. G Gregoriadis. 2nd ed. Boca Raton: CRC Press, Inc., 1992. III: 262–275.

94. Gould-Fogerite, S., and R. Mannino. 1996. Mucosal and systemic immunization using cochleate and liposome vaccines. J. of Liposome Res. 6: 357–379.

95. Dang, A., J. Phillips, and E. Raveche. 1996. Altered CD45 expression in malignant B-1 cells. Cell Immunol. 169: 196–207

96. Holmes, K. L., J. H. Pierce, W. F. Davidson, and H. G. Morse. 1986. Murine Hematopoietic Cells with Pre-B or Pre-B/Myeloid Characteristics are Generated by In Vitro Transformation with Retroviruses Contianing fes,ras,abl, and src Oncogenes. J. Exp. Med. 164: 443–457.

97. Nesterova, M., and, Y. S. Cho-Chung. 1995. A single injection protein kinase A directed antisense treatment to inhibit tumour growth. Nature Medicine. 1: 528–533.

98. Sanchez-Blazquez, P., A. Carcia-Espana, and J. Garzon. 1995. In vivo injection of antisense oligodecixynucleotides to G alpha subunits and supraspinal analgesia evoked by mu and delta opioid agonists. J. of Pharm. Exp. Therap. 275: 1590–1596.

99. Dean, N., R. McKay, L. Miraglia, R. Howard, S. Cooper, J. Giddings, P. Nicklin, L. Meister, R. Ziel, T. Geiger, M. Muller, and D. Fabbro. 1996. Inhibition of growth of lhuman tumor cell lines in nude mice by an antisense oligonucleotide inhibitor of protein kinase C-alpha expression. Canc. REs. 56: 3499–3507.

100. Raffa, R. B., C. Connelly, J. Chambers, and D. Stone. 1996. Alpha subunit G protein antisense oligo effects on icv in mice. Life Sci. 58: 77–80.

101. Raffa, R. B., R. P. Martinez, and C. D. Connelly. 1994. G protein antisense oligo and mu-opioi(d supraspinal anticociception. Eur. J. Phann. 258: R5–7.

102. Adams, J., X. Chen, J. DeRiel, M. Adler, and Y. Liu-Chen. 1994. ICV treatment with antisense oligo to kappa opioid receptors inhibited kappa agonist induced analgesia in rats. Brain Res. 667: 129–132.

103. Karle, J., and M. Nielsen. 1995. Modest reduction of benzodiazepine binding in rat brain in vivo induced by antisense oligo to GABAA receptor. Eur J Pharm. 291: 439–441.

104. Oberbauer, R. G. F. Schreiner, J. Biber, H. Murer, and T. W. Meyer. 1996. In vivo suppression of the renal Na+/Pi cotransporter by antisense oligonucleotides. PNAS. 93: 4903–4906.

105. Morishita, R., G. Gibbons, K. Ellison, M. Nakajima, L. Zhang, Y. Kaneda, T. Ogihara, and V. Dzau. 1993. Single intraluminal delivery of antisense cdc2 kinase and proliferating cell nuclear antigen oligo results in chronic inhibition of neointimal hyperplasia. *PNIAS*. 90: 8474–8478.

106. Ogo, H., H. Y., S. Miki, H. Nishio, M. Akiyama, and Y. Nakata. 1994. Modulation of substance P in human astrocytoma cells by antisense oligodeoxynucleotides. *Gen. Pharm.* . 25: 1131–1135.

107. Iversen, P. L., J. Mata, W. G. Tracewell, and G. Zon. 1994. Pharmacokinetics of an antisenes phophorothioate oligodeoxynculeotide against rev from HIV in adult male rat following single injections and continuous infusion. *Antisense Res. Dev*. 4: 43–52.

108. Ratajczak, M. Z., J. Kant, S. Luger, N. Hijiya, J. Zhang, G. Zon, and A. Gewirtz. 1992. In vivo treatment of human leukemia in a scid mouse model with c-myb antisense oligodeoxynucleotides. *PNAS*. 89: 11823–11827.

109. Beatty, P. R., S. M. Krams, and O. M. Martinez. 1997. Involvement of IL-10 in the Autonomous Growth of EBV-Transformed B Cell Lines. *J. Immunol*. 158: 4045–4051.

110. Raveche, E. S., A. D. Steinberg, L. W. Klassen, and J. H. Tjio. 1978. Genetic studies in NZB mice. I Spontaneous autoantibody production. *J Exp Med*. 147: 1487–1502.

111. Raveche, E. S., J. H. Tjio, and A. D. Steinberg. 1979. Genetic studies in NZB mice II. Hyperdiploidy in the spleen of NZB and their hybrids. *Cytogenet. Cell Genet*. 23: 182–193.

112. Raveche, E. S., J. H. Tjio, and A. D. Steinberg. 1980. Genetic studies in NZB mice: The effects of sex hormones on the spontaneous production of anti-T cells autoantibodies. *Arth Rheum*. 23: 48–56.

113. Raveche, E., E. Novotny, C. Hansen, J. Tjio, and A. Steinberg. 1981. Genetic studies in NZB mice V. Recombinant inbred lines demonstate that separate genes control autoimmune phenotype. *J. Exp Med*. 153: 1187–1197.

114. Miller, M., E. Raveche, C. Laskin, D. Klinman, C. A. Laskin, and A. D. Steinberg. 1984. Association of autoimmune traits in recombinant inbred lines. *J. Immunol*. 133: 1325–1331.

115. Chomarat, P., M.-C. Rissoan, J. Banchereau, and P. Miossec. 1993. Interferon g inhibits interleukin 10 production by monocytes. *J. Exp. Med*. 177: 523–527.

116. Buschle, M., D. Campana, S. Carding, C. Richard, A. V. Hoffbrand, and M. K. Brenner. 1993. Interferon-gamma inhibits apoptotic cell death in B CLL. *J.E.M*. 177: 213–218.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. An antisense oligodeoxynucleotide specific for interleukin-10 mRNA consisting of the formula 5'-TGGGTCTTGGTTCTCAGCTTGGGGCAT (SEQ ID NO: 1).

* * * * *